United States Patent
Kim et al.

(10) Patent No.: US 11,193,098 B2
(45) Date of Patent: *Dec. 7, 2021

(54) PCR APPARATUS COMPRISING REPEATED SLIDING MEANS AND PCR METHOD USING SAME

(71) Applicant: NANOBIOSYS INC., Seoul (KR)

(72) Inventors: Sung Woo Kim, Seoul (KR); Jae Young Byun, Anyang-si (KR); Eun-Sub Kim, Bucheon-si (KR); Duck Joong Kim, Anyang-si (KR)

(73) Assignee: NANOBIOSYS INC., Seoul (KR)

( * ) Notice: Subject to any disclaimer, the term of this patent is extended or adjusted under 35 U.S.C. 154(b) by 529 days.

This patent is subject to a terminal disclaimer.

(21) Appl. No.: 15/539,978

(22) PCT Filed: Dec. 22, 2015

(86) PCT No.: PCT/KR2015/014080
§ 371 (c)(1),
(2) Date: Jun. 26, 2017

(87) PCT Pub. No.: WO2016/105073
PCT Pub. Date: Jun. 30, 2016

(65) Prior Publication Data
US 2017/0342360 A1   Nov. 30, 2017

(30) Foreign Application Priority Data
Dec. 26, 2014  (KR) .................. 10-2014-0190168

(51) Int. Cl.
   *B01L 7/00*    (2006.01)
   *C12M 1/38*   (2006.01)
(Continued)

(52) U.S. Cl.
   CPC .............. *C12M 1/38* (2013.01); *B01L 7/00* (2013.01); *B01L 7/52* (2013.01); *B01L 7/5255* (2013.01);
(Continued)

(58) Field of Classification Search
   USPC .......................................... 435/286.1, 289.1
   See application file for complete search history.

(56) References Cited

U.S. PATENT DOCUMENTS

2001/0041357 A1* 11/2001 Fouillet ............ B01L 3/502784
                                                            435/91.1
2002/0102149 A1*  8/2002 Warhurst ................. B65G 1/10
                                                            414/267
(Continued)

FOREIGN PATENT DOCUMENTS

CN   101363001 A    2/2009
CN   101711257 A    5/2010
(Continued)

OTHER PUBLICATIONS

Kim et al., English machine transtion of KR 10-2012-0139205. (Year: 2012).*

*Primary Examiner* — Liban M Hassan
(74) *Attorney, Agent, or Firm* — Novick, Kim & Lee, PLLC; Sang Ho Lee

(57) ABSTRACT

A PCR apparatus comprises a PCR heating block having at least two heater units, wherein the at least two heater units are repeatedly disposed on one side of a substrate in a first direction, and each of the at least two heater units has two or more heaters; and a PCR chip having at least two reaction chambers, wherein the at least two reaction chambers are repeatedly formed in the PCR chip, and when the PCR chip is in contact with the PCR heating block, the at least two reaction chambers are arranged to be contacted with the at least two heater units on the PCR heating block, wherein the
(Continued)

PCR chip is repeatedly moved in a back-and-forth direction parallel to the first direction and the at least two reaction chambers of the PCR chip is placed to be in contact with the at least two heater units of the PCR heating block.

16 Claims, 19 Drawing Sheets

(51) Int. Cl.
  *C12Q 1/68* (2018.01)
  *C12Q 1/686* (2018.01)
(52) U.S. Cl.
  CPC ............... *C12Q 1/68* (2013.01); *C12Q 1/686* (2013.01); *B01L 2200/143* (2013.01); *B01L 2300/0627* (2013.01); *B01L 2300/0829* (2013.01); *B01L 2300/1805* (2013.01)

(56) References Cited

U.S. PATENT DOCUMENTS

| 2007/0098600 A1* | 5/2007 | Kayyem | B01L 3/5027 422/400 |
| 2012/0295312 A1 | 11/2012 | Seo et al. | |
| 2013/0040377 A1* | 2/2013 | Kim | C12Q 1/686 435/287.2 |
| 2013/0053272 A1 | 2/2013 | Joseph et al. | |
| 2013/0230860 A1 | 9/2013 | Park et al. | |
| 2014/0065703 A1 | 3/2014 | Dale et al. | |
| 2017/0008000 A1 | 1/2017 | Kim | |

FOREIGN PATENT DOCUMENTS

| CN | 105940097 A | | 9/2016 | |
| JP | 2013-524808 A | | 6/2013 | |
| JP | 2013-208067 A | | 10/2013 | |
| KR | 10-2010-0030825 A | | 3/2010 | |
| KR | 20110118572 A | * | 10/2011 | ............ C12Q 1/686 |
| KR | 20120139205 A | * | 12/2012 | |
| KR | 10-2013-0065337 A | | 6/2013 | |
| KR | 10-2014-0029627 A | | 3/2014 | |
| KR | 10-1456646 B1 | | 11/2014 | |
| WO | 2014/104771 A1 | | 7/2014 | |
| WO | 2014148800 A1 | | 9/2014 | |

* cited by examiner

PCR APPARATUS COMPRISING REPEATED SLIDING MEANS AND PCR METHOD USING SAME

TECHNICAL FIELD

The present invention relates to a PCR apparatus having a PCR heating block in which heaters are repeatedly arranged and a PCR chip in which reaction chambers are repeatedly formed and to a PCR method using the same.

BACKGROUND ART

Polymerase Chain Reaction (hereinafter, referred to as 'TCR') is a technique wherein a specific portion of a template nucleic acid is repeatedly heated and cooled, the specific portion is successively replicated, and the nucleic acid having the specific portion is amplified exponentially. The PCR is widely used for the purposes of analysis and diagnosis in various fields like biotechnology, genetic engineering, medicine and so on. Recently, a variety of apparatuses for efficiently performing PCR have been developed.

According to a conventional PCR apparatus, PCR is performed by a reaction vessel having a plurality of tubes in which sample solutions including template nucleic acids are contained is mounted on a single heater, and the reaction vessel is repeatedly heated and cooled (See FIGS. 1 and 2). Since the conventional PCR apparatus has one heater, in this case, it is not complicated in structure and introduces a plurality of samples therein to increase the density of samples. However, the conventional PCR apparatus has to have a complicated circuit for accurately controlling temperatures. Since the size of the tube-shaped reaction vessel is relatively large, further, a large amount of sample is needed, and the reaction vessel is repeatedly heated or cooled through one heater, thereby undesirably extending total PCR time.

According to another conventional PCR apparatus, further, PCR is performed by mounting a plurality of heaters having a PCR temperature and flowing a sample solution having the a nucleic acid along one channel passing through each of the heaters (See FIG. 3). Since the conventional PCR apparatus has the plurality of heaters set to the PCR temperatures, in this case, there is no need to repeatedly carry out heating and cooling of the reaction vessel through the heaters, thereby advantageously shortening PCR time. Since the conventional PCR apparatus has the plurality of heaters, further, it can have a relative simple circuit configuration, but it has to have a long channel passing through the high temperature heaters and the low temperature heaters, thereby undesirably making the whole configuration complicated and making it difficult to apply a plurality of samples. Further, a controller is additionally needed to control the flow rate of the sample solution having the nucleic acid flowing along the channel passing through the heaters, thereby undesirably making it hard to increase the densities of sample and apparatus.

Recently, there have been proposed PCR apparatuses capable of not only increasing PCR yield and recognizing a PCR process in real time, but also increasing the density of samples to handle a large number of samples in a one time PCR process, and reducing PCR time to increase the throughput of samples. In this case, there is a still need for the development of a new PCR apparatus having a technique capable of accurately controlling set temperatures of the heaters arranged in parallel with each other and are not repeatedly heated and cooled to greatly reduce the PCR time and a technique capable of conveying a large number of samples using the heaters having the set temperatures to at the same time perform the PCR for the samples.

DISCLOSURE

Technical Problem

Accordingly, the present invention has been made in view of the above-mentioned problems occurring in the prior art, and it is an object of the present invention to provide a PCR apparatus that is capable of improving PCR time, PCR yield and throughput of samples, achieving miniaturization and portability thereof, and providing real-time measurement and analysis.

Technical Solution

To accomplish the above-mentioned object, according to the present invention, a PCR apparatus is provided including: a PCR heating block having two or more heaters repeatedly spaced apart from each other on top of a substrate; a plate-shaped PCR chip having two or more reaction chambers repeatedly formed thereon in such a manner as to come into contact with the two or more heaters arranged on the PCR heating block upon the thermal contact with the PCR heating block; and repeated sliding means adapted to repeatedly slide in forward and backward directions in such a manner as to maintain the contact between the PCR chip and the PCR heating block in the state of mounting the PCR chip thereon, so that upon the repeated sliding, thermal contacts between the reaction chambers formed on the PCR chip and the heaters arranged on the PCR heating block are repeatedly performed.

According to the present invention, desirably, the adjacent heaters among the two or more heaters may be implemented at different temperatures.

According to the present invention, desirably, among the two or more heaters, a first heater located on one end of the PCR heating block has a temperature of a PCR denaturing step and a second heater thereof has a temperature of an annealing and extension (or amplification) step.

According to the present invention, desirably, the two or more reaction chambers of the PCR chip are spaced apart from each other in a sliding direction of the PCR chip or in a vertical direction with respect to the sliding direction of the PCR chip, and otherwise, the two or more reaction chambers have the shapes of channels continuously passing through the PCR chip in a vertical direction with respect to the sliding direction of the PCR chip.

According to the present invention, desirably, the two or more reaction chambers of the PCR chip have the shapes of inlet/outlet integrated type wells or the shapes of inlet/outlet separate type channels.

According to the present invention, desirably, the PCR apparatus further includes: light sources adapted to provide light to the two or more reaction chambers of the PCR chip; and light detectors adapted to accommodate the light emitted from the light sources therein.

According to the present invention, desirably, the light sources or the light detectors are repeatedly arranged on the spaces between the adjacent heaters of the PCR heating block.

According to the present invention, desirably, the light sources or the light detectors move correspondingly to the moving path of the PCR chip.

According to the present invention, desirably, the PCR apparatus further includes a chip stand-by part adapted to accommodate a plurality of PCR chips drivedly connected with each other therein so that after a first PCR chip comes into thermal contact with the PCR heating block, a second PCR chip starts thermal contacting with the PCR heating block.

Advantageous Effects

According to the present invention, the PCR apparatus can perform the PCR rapidly and accurately through the repeated thermal contacts between the heating block having the two or more heaters having PCR temperatures in such a manner as to be repeatedly arranged thereon and the PCR chip having the two or more reaction chambers formed thereon and can at the same time perform the PCR for a plurality of samples to improve the throughput of the samples. According to the present invention, further, the PCR apparatus can prevent the radial thermal distribution generated from the individual heaters and the non-uniform heat superposition between the adjacent heaters to improve PCR yield and further can require no separate temperature control means to achieve the miniaturization and integration of the apparatus. According to the present invention, furthermore, the PCR apparatus can amplify a plurality of nucleic acid samples at the same time and rapidly by using the PCR heating block on which the heaters are repeatedly arranged and the plate-shaped PCR chip and also can measure successively generated optical signals or electrochemical signals to in real time check the process of nucleic acid amplification.

MODE FOR INVENTION

Hereinafter, embodiments according to the present invention will be described in detail given with reference to the attached drawing. Before the present invention is disclosed and described, however, it is to be understood that the disclosed embodiments are merely exemplary of the invention, which can be embodied in various forms.

According to the present invention, PCR (Polymerase Chain Reaction) refers to a kind of reaction for amplifying nucleic acids having a specific sequence. For example, in order to amplify DNA (deoxyribonucleic acid) having specific sequence, a PCR apparatus performs a denaturing step wherein a solution containing PCR sample and reagent in which double-stranded DNA as template nucleic acid is contained is heated to a given temperature, for example, about 95° C. and the double-stranded DNA is separated to single-stranded DNA, an annealing step wherein an oligonucleotide primer having a complementary sequence to the sequence of the DNA to be amplified is provided and cooled to a given temperature, for example, 55° C., together with the separated single-stranded DNA, and the primer is then bonded to the specific sequence of the single-stranded DNA to form a partial DNA-primer composite, and an extension (amplification) step wherein the solution is maintained to an appropriate temperature, for example, 72° C. after the annealing step and double-stranded DNA is formed on the basis of the primer of the partial DNA-primer composite by means of DNA polymerase. In this case, the three steps are repeatedly performed 20 to 40 times to allow the DNA having the specific sequence to be amplified exponentially. In some cases, the PCR apparatus performs the annealing step and the extension (or amplification) step, at the same time, and at this time, the PCR apparatus performs two steps including the denaturing step and the annealing and extension step, thereby finishing a first cycle. Accordingly, a PCR heating block and a PCR apparatus having the same according to the present invention include modules for performing the above-mentioned steps, and detailed modules not described herein have been disclosed in conventional techniques for PCR or within the obvious scope of the present invention.

Figure 1:
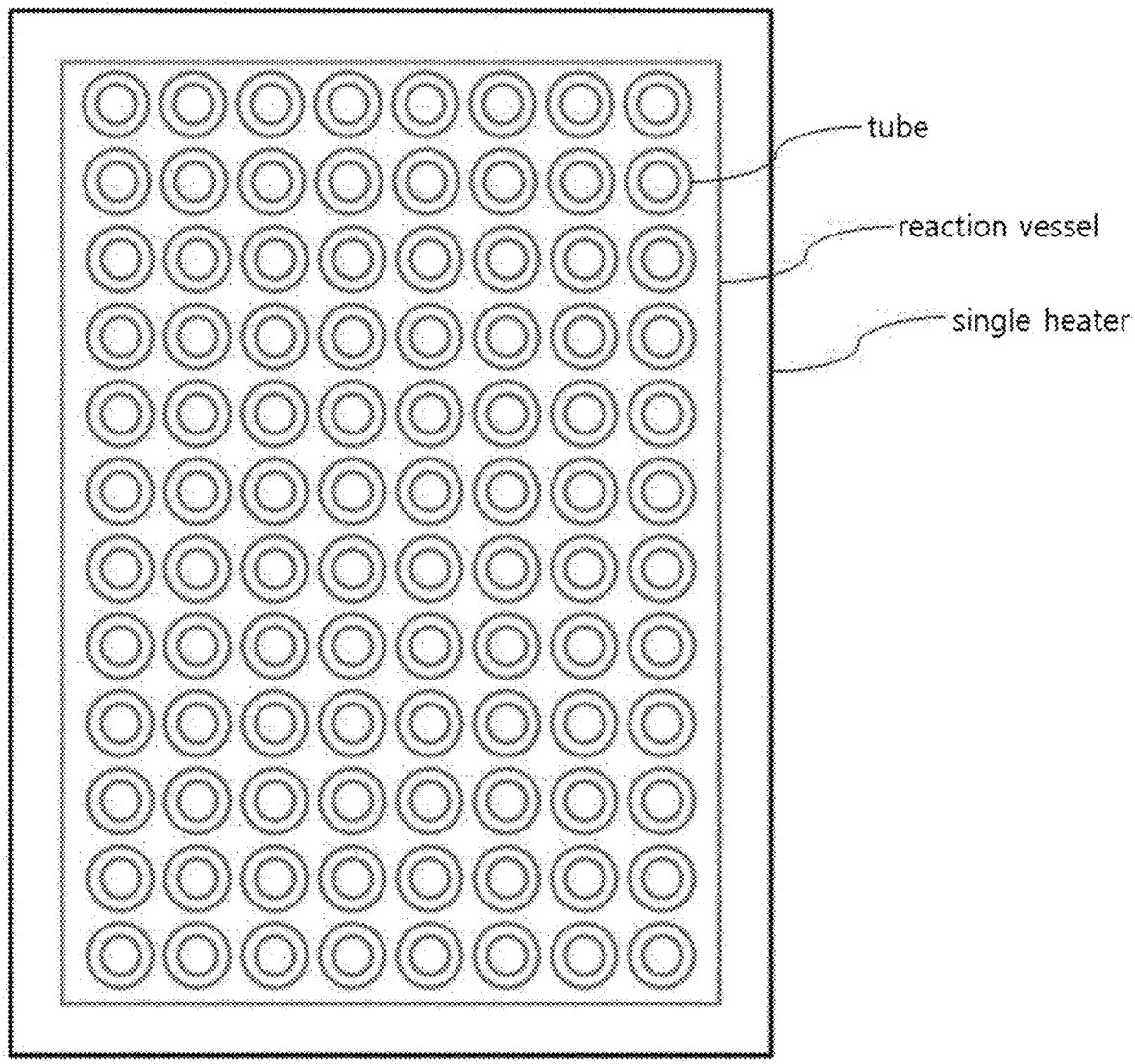
FIGS. 1 and 2 are top and axial sectional views showing an existing single heater type PCR heating block and a tube type PCR reaction vessel mounted on the PCR heating block.
Figure 2:
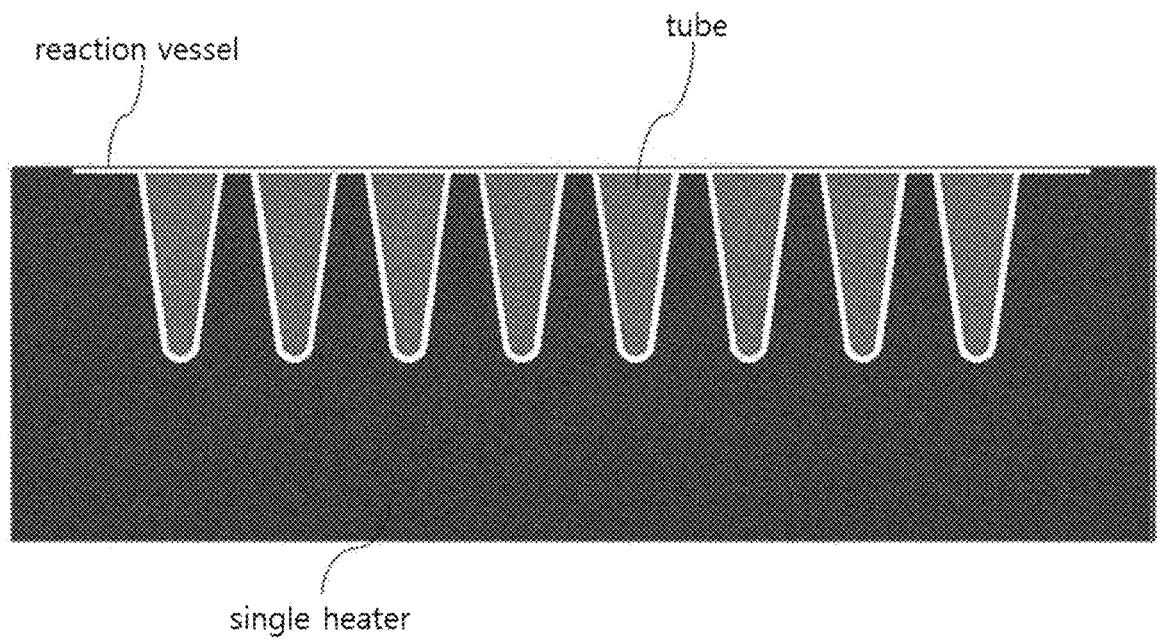
Figure 3:
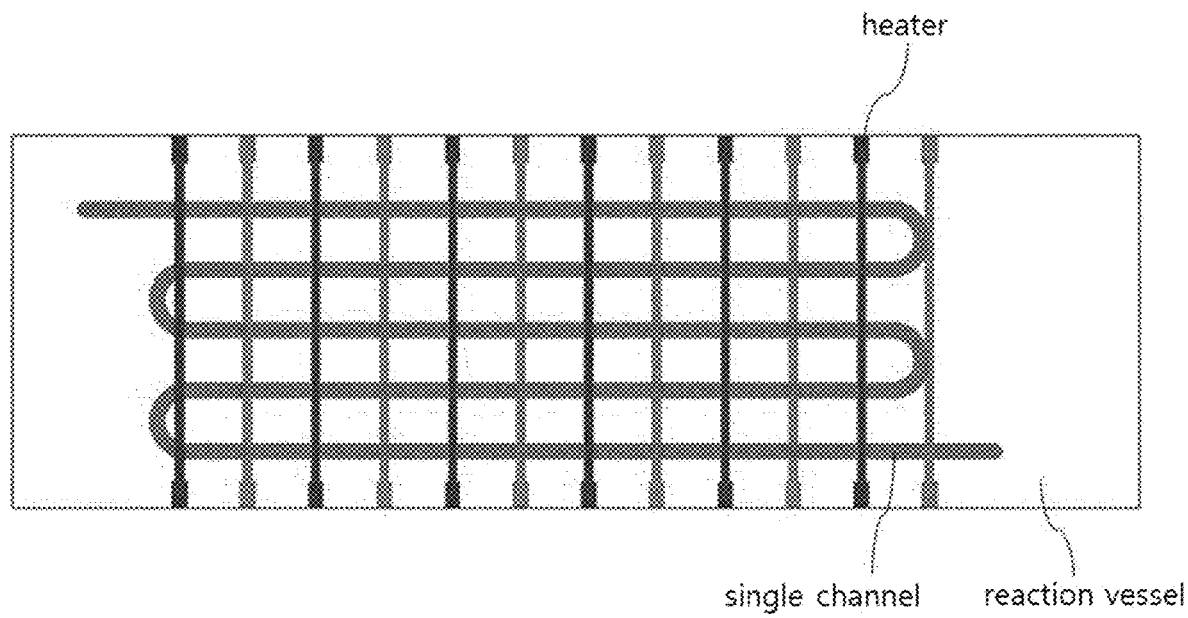
FIG. 3 is a top view showing an existing multiple heater type PCR heating block and a channel type PCR reaction vessel mounted on the PCR heating block.
Figure 4:
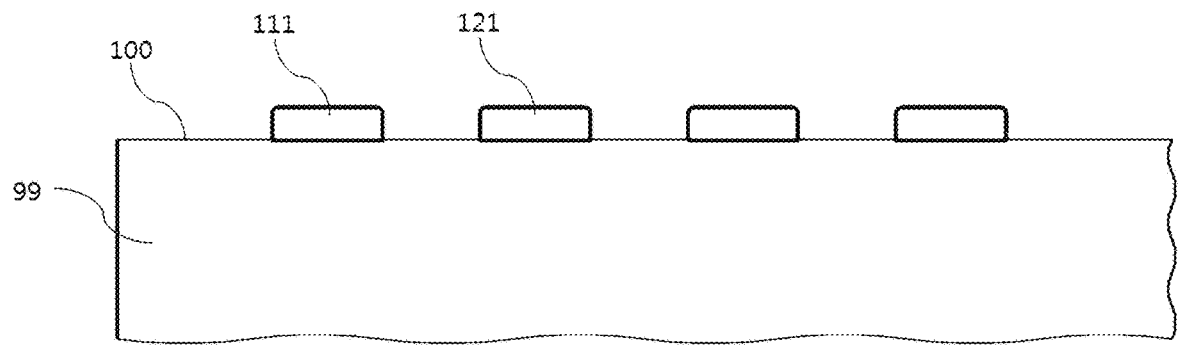
FIG. 4 is a sectional view showing a PCR apparatus according to the present invention, wherein a PCR heating block 100 is disposed on top of a substrate 99 and has two or more heaters 111 and 121 repeatedly spaced apart from each other thereon.

FIG. 4 is a sectional view showing a PCR apparatus according to the present invention, wherein a PCR heating block 100 is disposed on top of a substrate 99 and has two or more heaters 111 and 121 repeatedly spaced apart from each other thereon.

As shown in FIG. 4, the PCR heating block 100 has the two or more heaters 110 and 120 repeatedly arranged thereon to supply heat to PCR solutions. The PCR heating block 100, which is a module keeping a given temperature, includes a contacted surface with a PCR reaction region formed on at least one surface thereof, so that through the heat contact, the heat is supplied to the PCR solutions (including samples and reagents for performing PCR), thereby performing the PCR. The substrate 99 is made of a material which is not changed in physical or chemical properties due to the heating of the heaters 110 and 120 arranged on the surface thereof and causes no heat exchanging between the two or more heaters 110 and 120. For example, the substrate 99 is made of a material like plastic, glass and silicone, and if necessary, it may be transparent or translucent. To achieve miniaturization and integration of the PCR apparatus, the PCR heating block 100 has a shape of a generally thin plate having a thickness in the range of about 50 nm to 1 mm, desirably, a thickness of about 250 μm. However, the thickness of the PCR heating block 100 is not limited to the range as mentioned above.

The two or more heaters 110 and 120 are repeatedly spaced apart from each other on the PCR heating block 100, and for example, the two or more heaters 110 and 120 of the PCR heating block 100 are configured wherein a first cycle of PCR starts at the heater located at one end of the PCR heating block 100 and a final cycle of PCR is finished at the heater located at the other end of the PCR heating block 100. Further, the PCR heating block 100 has various shapes for efficiently supplying heat to the PCR reaction region, such as a plane, channel, or pillar capable of increasing a surface to volume ratio.

The heaters 110 and 120 are conductive heating elements arranged on the substrate 99 and may be formed of heaters using Joule heating or thermoelectric elements causing Peltier effect. The adjacent heaters among the two or more heaters 110 and 120 of the PCR heating block 100 have different temperatures from each other, and the temperature pattern between the adjacent heaters is repeated through the combination of a given number of heaters. For example, a first heater has a temperature of 95° C., a second heater has a temperature of 55° C., and a third heater has a temperature of 72° C. In this case, such temperature pattern is repeated 10 times, 20 times, 30 times or 40 times. Otherwise, the first heater has a temperature of 95° C., and the second heater has a temperature of 72° C. In this case, such temperature pattern is repeated 10 times, 20 times, 30 times or 40 times. The two or more heaters 110 and 120 of the PCR heating block 100 are configured wherein the first cycle of PCR starts at the heater (having a temperature of 95° C.) located at one end of the PCR heating block 100 and the final cycle of PCR is finished at the heater (having a temperature of 72° C.) located at the other end of the PCR heating block 100.

The heaters 110 and 120 are connected to a power module and a control module so as to maintain given temperatures and also connected to sensors for monitoring the temperatures of the heaters. So as to allow the internal temperatures of the heaters 110 and 120 to be constantly maintained, unit electrodes, that is, heater electrodes are symmetrically arranged in up and down and/or left and right directions around the center points of the surfaces of the heaters. So as to achieve rapid heat transmission and high conductivity, further, the heaters 110 and 120 are made of one or more materials selected from the group consisting of chrome, aluminum, copper, iron, silver and carbon, or made of their composite materials. However, the materials of the heaters are not limited to those as mentioned above. Furthermore, the heaters 110 and 120 may include one or more materials selected from the group consisting of conductive nanoparticles containing light transmission heating elements, for example, an oxide semiconductor and a material to which impurities selected from the group consisting of In, Sb, Al, Ga, C and Sn are added to the oxide semiconductor, indium tin oxide, conductive polymer, carbon nanotube, and graphene.

In case where the heaters 110 and 120 are two times arranged on the top of the PCR heating block 100, the PCR time required for the two steps for PCR, that is, the denaturing step and the annealing/extension step is shorter than that required for the three steps for the PCR, that is, the denaturing step, the annealing step, and the extension step for PCR, and further, the number of heaters is reduced, thereby improving the simplification and density of the structure. In the three steps for PCR, on the other hand, the temperature of the denaturing step is in the range of 85 to 105° C., desirably 95° C., the temperature of the annealing step is in the range of 40 to 60° C., desirably 50° C., and the temperature of the extension step is in the range of 50 to 80° C., desirably 72° C. In the two steps for PCR, furthermore, the temperature of the denaturing step is in the range of 85 to 105° C., desirably 95° C., and the temperature of the annealing/extension step is in the range of 50 to 80° C., desirably 72° C. However, the given temperatures and the ranges of the given temperatures for the PCR may be of course adjustable in the range known.

As mentioned above, the two or more heaters 110 and 120 maintaining the given temperatures are repeatedly arranged on the PCR heating block 100, thereby increasing a temperature to time ratio. According to the existing single heater type PCR apparatus, for example, the temperature to time ratio is in the range of 3 to 7° C. per second, and according to the PCR apparatus of the present invention wherein the heaters are repeatedly arranged, contrarily, the temperature to time ratio between the heaters is in the range of 20 to 40° C. per second, thereby greatly shortening the time for PCR. According to the PCR apparatus of the present invention wherein the heaters are repeatedly arranged, the temperatures at the denaturing step, the annealing step, and the extension step (or the denaturing step and the annealing/extension step) can be accurately controlled, and further, it is possible to maintain desired temperatures or temperature ranges only at portions at which heat is supplied from the heaters. Also, various numbers of heaters are repeatedly arranged on the PCR heating block 100, thereby achieving various PCR cycle times. For example, in case of the PCR having 10 cycle times, 20 or 30 heaters are repeatedly arranged. According to intended PCR cycle times, that is, the heaters can be repeatedly arranged 10, 20, 30, 40 or 50 times on the PCR heating block 100.

Figure 5:
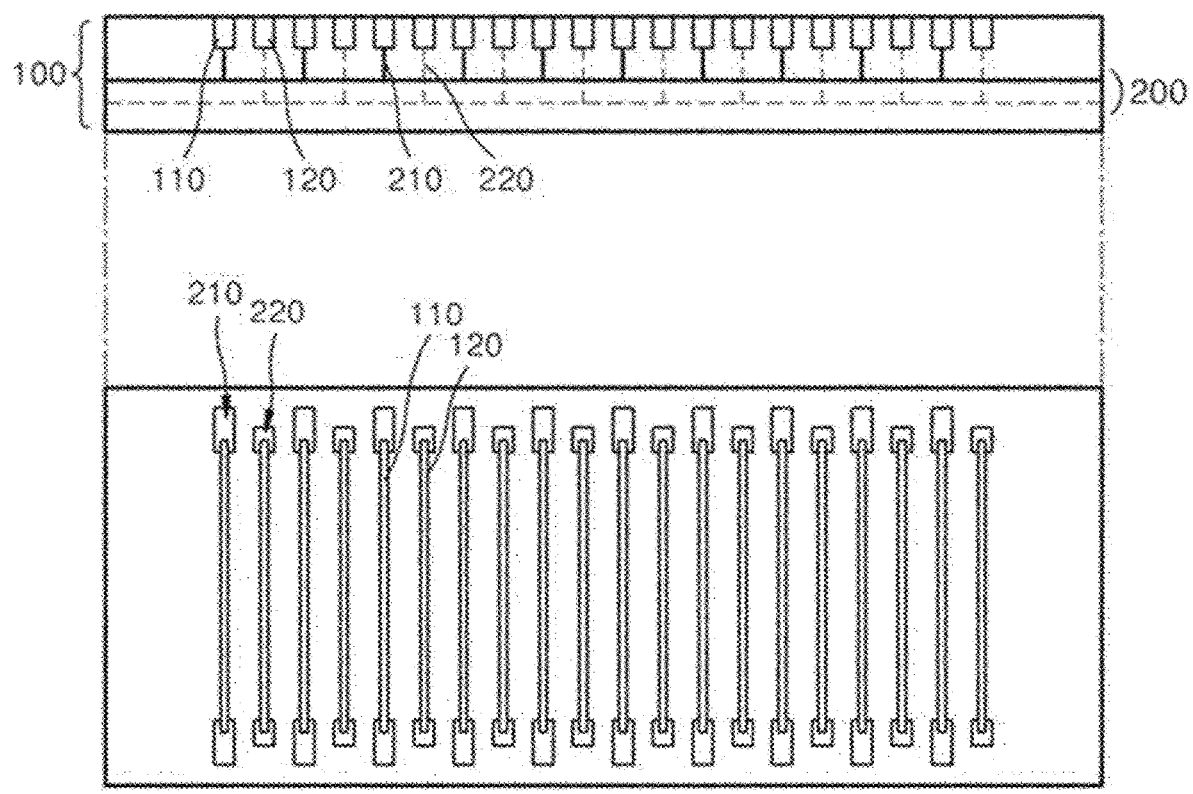
FIG. 5 is a top view showing the arrangement of the heaters of the PCR heating block of the PCR apparatus according to the present invention.

FIG. 5 shows the PCR heating block 100 according to the present invention and a power supply part 200 for supplying power to the heaters repeatedly arranged on the PCR heating block 100. In more detail, the upper end portion of FIG. 5 shows a vertical sectional view of the PCR heating block 100, and the lower end portion of FIG. 5 shows a top view of the PCR heating block 100. As shown in FIG. 5, the PCR heating block 100 includes 20 heaters repeatedly arranged thereon. The power supply part 200 is a module which supplies power to the PCR heating block 100 from a power supply source and heats the PCR heating block 100 and includes first and second distributed wires 210 and 220 adapted to distribute power to the heaters 110 and 120. As shown in FIG. 5, for example, the first distributed wire 210 of the PCR heating block 100 is located to supply power to the first heaters 110, and the second distributed wire 220 of the PCR heating block 100 is located to supply power to the second heaters 120. If the first heaters 110 maintain a temperature of the PCR denaturing step, for example, a temperature of 85 to 105° C. and the second heaters 120 maintain a temperature of the PCR annealing/extension step, for example, a temperature of 50 to 80° C., the first distributed wire 210 receives the power for maintaining the temperature of the PCR denaturing step from the power supply part 200 and the second distributed wire 220 receives the power for maintaining the temperature of the PCR annealing/extension step from the power supply part 200. The first distributed wire 210 and the second distributed wire 220 are made of a conductive material like gold, silver, copper and so on, but they are not limited thereto. The power supply sources (not shown) are modules for supplying power to the power supply part 200 in such a manner as to be connected correspondingly to the first distributed wire 210 and the second distributed wire 220 of the power supply part 200. While the PCR is being performed, for example, a first power port (not shown) of the power supply sources is electrically connected to the first distributed wire 210, and a second power port (not shown) of the power supply sources is electrically connected to the second distributed wire 220. After that, if a command for performing the PCR is issued from a user, the power supply sources supply power to the first distributed wire 210 and the second distributed wire 220 and rapidly heat the first heaters and the second heaters of the PCR heating block 100. If the heaters reach given temperatures, further, the power supply sources control the quantity of power supplied to allow the heaters to maintain their given temperatures.

Figure 6:
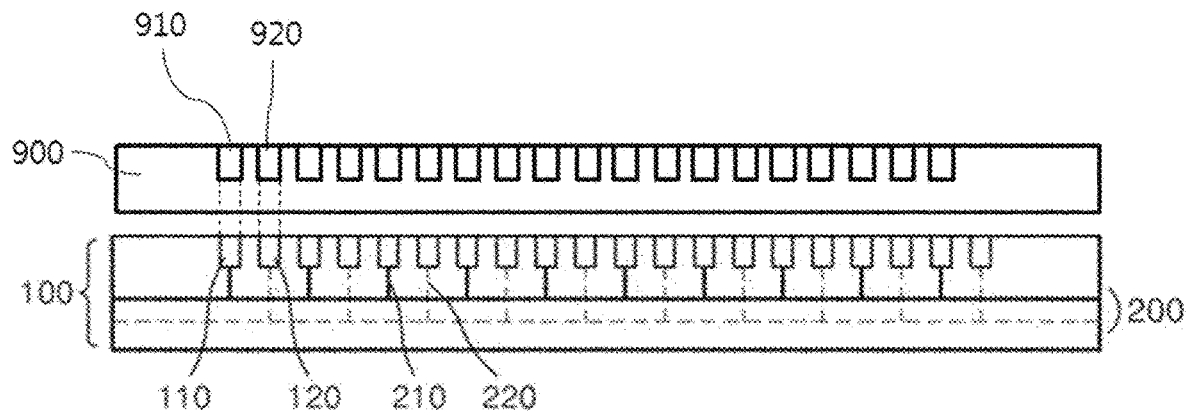
FIG. 6 is a sectional view showing a PCR chip 900 and two or more reaction chambers 910 formed in the PCR chip in the PCR apparatus according to the present invention.
Figure 7:
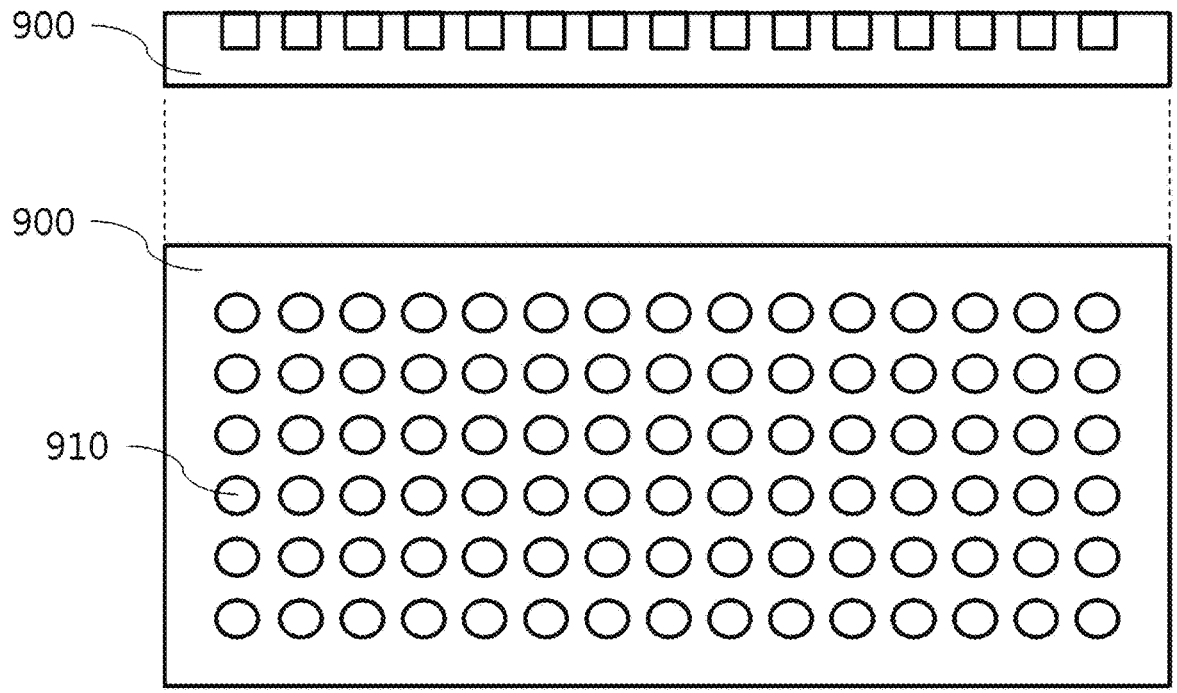
FIGS. 7 to 9 are sectional and top views showing various types of PCR chips 900 in the PCR apparatus according to the present invention.
Figure 8:
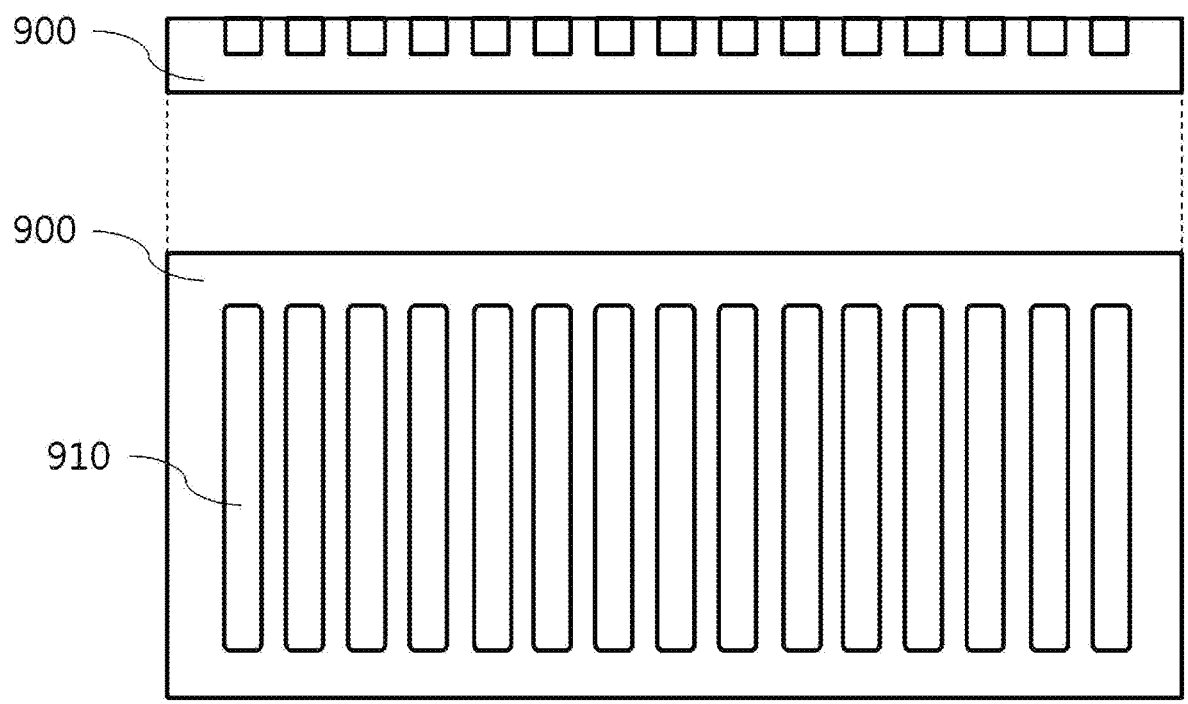
Figure 9:
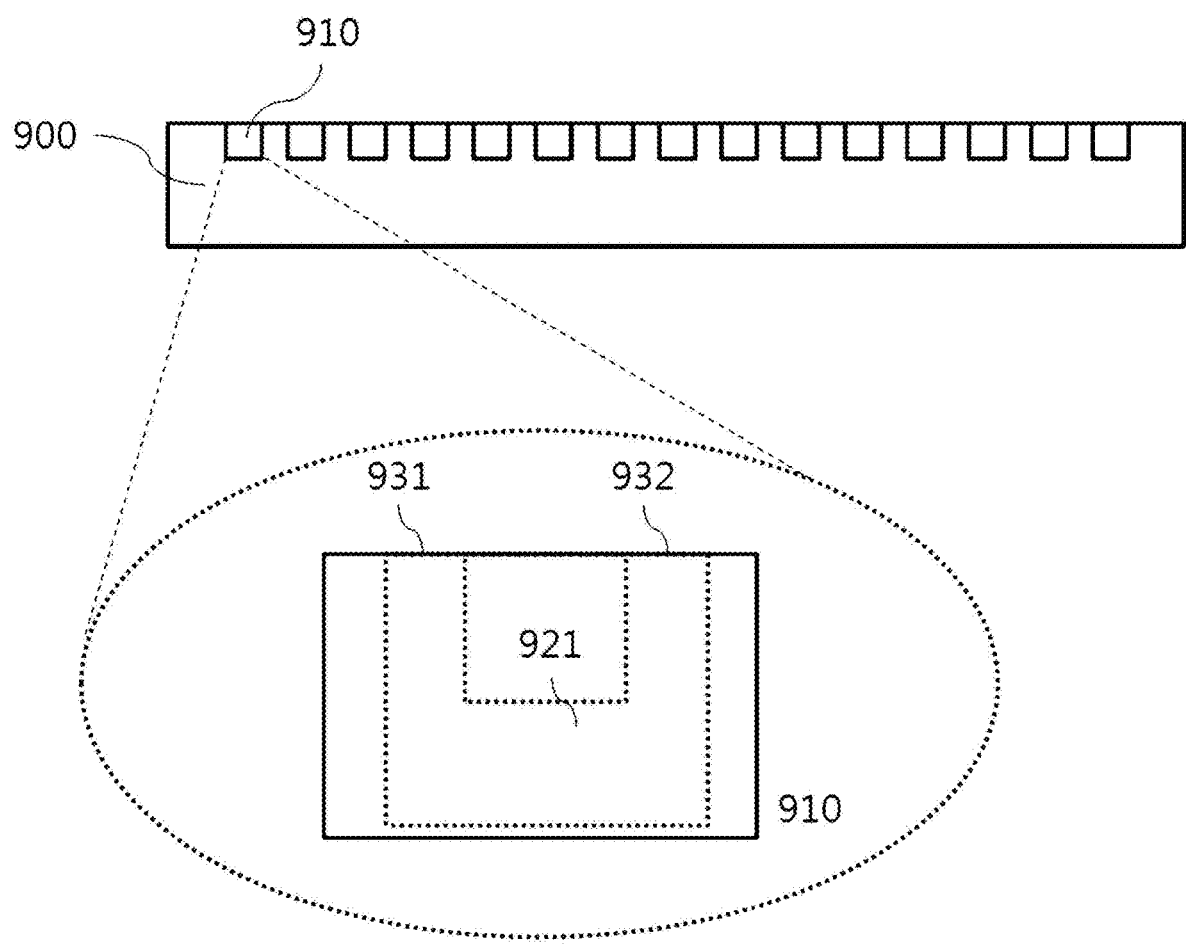

FIG. 6 is a sectional view showing a PCR chip 900 and two or more reaction chambers 910 formed in the PCR chip in the PCR apparatus according to the present invention, and FIGS. 7 to 9 are sectional and top views showing various types of PCR chips 900 in the PCR apparatus according to the present invention.

According to the present invention, as shown in FIG. 6, the PCR chip 900 has a shape of a plate and comes into a contact with the top of the PCR heating block 100, in more detail, with the heaters 110 and 120, and further, the PCR chip 900 includes two or more reaction chambers 910 and 920 repeatedly formed therein to come into contact with the two or more heaters 110 and 120. Under the above-mentioned configuration, FIGS. 7 to 9 show various types of PCR chips 900 in the PCR apparatus according to the present invention.

Each reaction chamber is a space for accommodating a solution therein, and the solution contains PCR sample and reagent having template nucleic acid double-stranded DNA to amplify DNA (deoxyribonucleic acid) having a specific sequence. According to the present invention, the reaction chambers are desirably formed in such a manner as to be disposed on the heater regions of the PCR heating block 100 upon the thermal contact with the PCR heating block 100 to perform the PCR. The number of reaction chambers is not particularly limited, but is preferably one more than the number of heaters of the PCR heating block 100. On the other hand, since the PCR chip 900 has a shape of a general plate, heat applied from the heaters can be uniformly transferred to each of the reaction chambers when they are in thermal contact with the PCR heating block 100.

As shown in FIG. 7, two or more reaction chambers 910 are repeatedly arranged on the plate-shaped PCR chip 900. Further, two or more reaction chambers 910 are arranged in a longitudinal direction of the PCR chip 900 or in a vertical direction with respect to the longitudinal direction of the PCR chip 900. In this case, the reaction chambers 910 have the same or different PCR sample and reagents as or from each other, so that the PCR for two or more kinds of samples or various kinds of samples through one PCR chip 900 can be performed.

As shown in FIG. 8, two or more reaction chambers 910 are repeatedly arranged on the plate-shaped PCR chip 900 and have shapes of channels formed continuously in a vertical direction with respect to a longitudinal direction of the PCR chip 900. In this case, the reaction chambers 910 have the same or different PCR sample and reagents as or from each other, so that the PCR for two or more kinds of samples or various kinds of samples through one PCR chip 900 can be performed.

On the other hand, as shown in FIGS. 7 and 8, the reaction chambers 910 of the PCR chip 900 have shapes of inlet/outlet integrated type wells, without any distinction of the inlet/outlet thereof, but contrarily, as shown in FIG. 9, the reaction chambers 910 of the PCR chip 900 have shapes of inlet/outlet separate type channels wherein an inlet 931 and an outlet 932 of each reaction chamber 910 are formed separately from each other on the unit region thereof in such a manner as to be connected with each other by means of one channel 921. In case of the existing multiple well plate-shaped PCR chip, the volume of sample is large to decrease the surface to volume ratio, so that the PCR time is extended, but according to the present invention, the inlet/outlet separate type channel-shaped PCR chip increases the surface to volume ratio, so that the PCR time is substantially shortened. A channel height of the reaction chamber 910 is in the range between 0.01 μm and 5 mm, but so as to increase the surface to volume ratio, desirably, the channel height thereof is lowered.

According to the present invention, on the other hand, the PCR chip 900 includes a first plate coming into contact with the PCR heating block 100, a second plate disposed on top of the first plate and having the two or more reaction chambers 910, and a third plate disposed on top of the second plate and having the inlets and outlets of the two or more reaction chambers 910. Accordingly, the PCR chip 900 has a plate-laminated structure, thereby providing a simple manufacturing process and a low manufacturing cost and achieving the increment of the heat exchange region with the PCR heating block 100. According to the present invention, the PCR chip 900 may be made of various materials, and desirably, it is made of a plastic thin film. Further, the PCR chip 900 is made of a light transmissive material, and if it is used for real-time PCR based on optical measurements like fluorescence, phosphorescence, luminescence, Raman spectroscopy, surface enhanced Raman scattering and surface Plasmon resonance, the PCR chip 900 is desirably made of a light transmissive material.

The first plate is bonded or attached to the PCR heating block 100 and receives heat from the PCR heating block 100. The first plate may be made of various materials, and desirably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, a hydrophilic substance (not shown) is applied to the top surface of the first plate which allows the PCR to be performed smoothly. Through the application of the hydrophilic substance, accordingly, a single layer containing the hydrophilic substance is formed on the first plate. The hydrophilic substance may include various materials, and desirably, it includes a material selected from the group consisting of carboxyl group (—COOH), amine group (—NH2), hydroxyl group (—OH), and sulfone group (—SH). The application of the hydrophilic substance is performed in a manner known in the art.

The second plate is disposed on top of the first plate. The second plate has the two or more reaction chambers. Accordingly, a target sample solution to be amplified is introduced into the two or more reaction chambers, and next, the PCR is performed. The second plate may be made of various materials, and desirably, it is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. Further, the second plate may have various thicknesses, and preferably, it has a thickness of 0.01 µm to 5 mm. The reaction chambers may have various widths and lengths, and preferably, have a width of 0.001 mm to 10 mm and a length of 1 mm to 400 mm. Furthermore, the inner wall of the second plate is coated with a material like silane group, bovine serum albumin (BSA) and so on so as to prevent DNA and protein from being absorbed thereto. The application of the material is performed in a manner known in the art.

The third plate is disposed on top of the second plate. The third plate has the inlets or outlets formed on the two or more reaction chambers formed on the second plate. Each inlet is a portion into which the target sample solution containing the nucleic acid to be amplified is introduced, and each outlet is a portion through which the target sample solution is discharged after the completion of the PCR. As mentioned above, the inlets and outlets may be integrated or separated with/from each other, and the internal surfaces of the inlets and outlets are continuously connected to the internal surfaces of the two or more reaction chambers. On the other hand, the third plate may be made of various materials, and desirably, it is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. Further, the inlet may have various sizes, and preferably, it has a diameter of 0.001 to 10 mm. Furthermore, the outlet may have various sizes, and preferably, it has a diameter of 0.001 to 10 mm. In addition, cover means are additionally mounted on the inlet and the outlet so as to prevent the target sample solution from leaking from the two or more reaction chambers when the PCR for the target sample solution is performed. The cover means may have various shapes, sizes or materials. Further, the third plate may have various thicknesses, and preferably, it has a thickness of 0.001 to 10 mm.

According to the present invention, the PCR chip 900 is easily made through a method including the steps of: providing the third plate having the inlets or outlets formed by means of machining; forming two or more reaction chambers by means of machining over portions corresponding to the inlets or outlets of the third plate on a plate having the corresponding size to the underside surface of the third plate to provide the second plate; forming a surface containing the hydrophilic substance by means of surface treatment on the top surface of a plate having the corresponding size to the underside surface of the second plate to provide the first plate; and bonding the underside surface of the third plate to the top surface of the second plate and bonding the underside surface of the second plate to the top surface of the first plate.

The inlets or outlets of the third plate and the two or more reaction chambers of the second plate are formed by means of a machining method selected from the group consisting of injection molding, hot-embossing, casting, and laser ablation. Further, the hydrophilic substance on the surface of the first plate is applied to the first plate by means of a method selected from the group consisting of oxygen and argon plasma treatment, corona discharge, and surface active agent coating, and the application of the hydrophilic substance is performed in a manner known in the art. Also, the bonding of the underside surface of the third plate to the top surface of the second plate and the bonding of the underside surface of the second plate to the top surface of the first plate are performed by means of thermal bonding, ultrasonic welding, solvent bonding, hot plate welding, ultraviolet bonding, and press bonding, and the bonding is performed in a manner known in the art. Further, a double-sided adhesive, a thermoplastic resin or a thermosetting resin may be applied to the spaces between the third plate and the second plate and between the second plate and the first plate.

Figure 10:
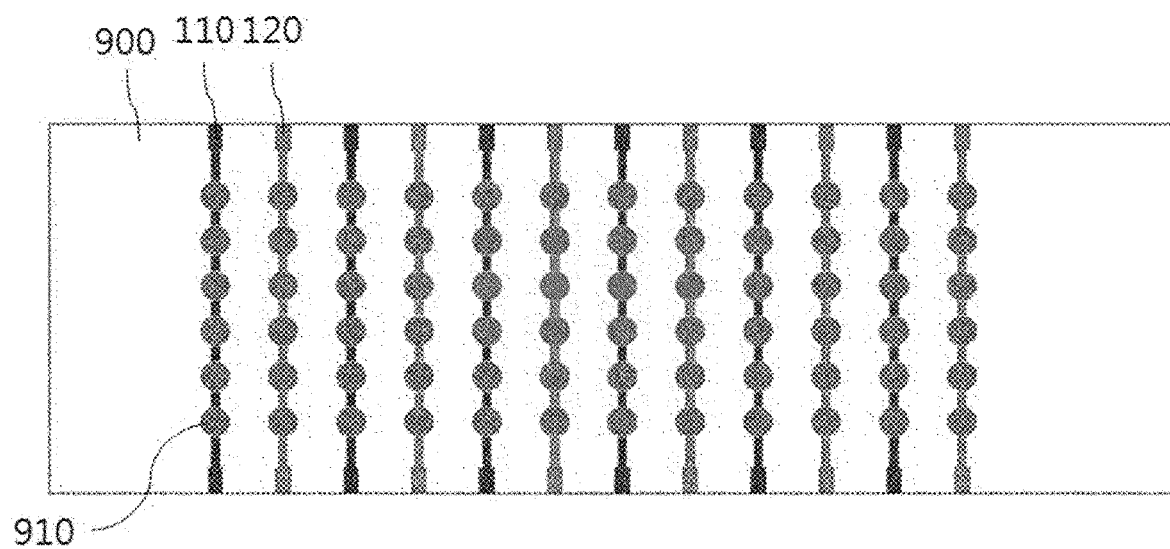
FIGS. 10 to 12 are top views showing the contacted states between the various types of PCR chip 900 and the PCR heating block in the PCR apparatus according to the present invention.
Figure 11:
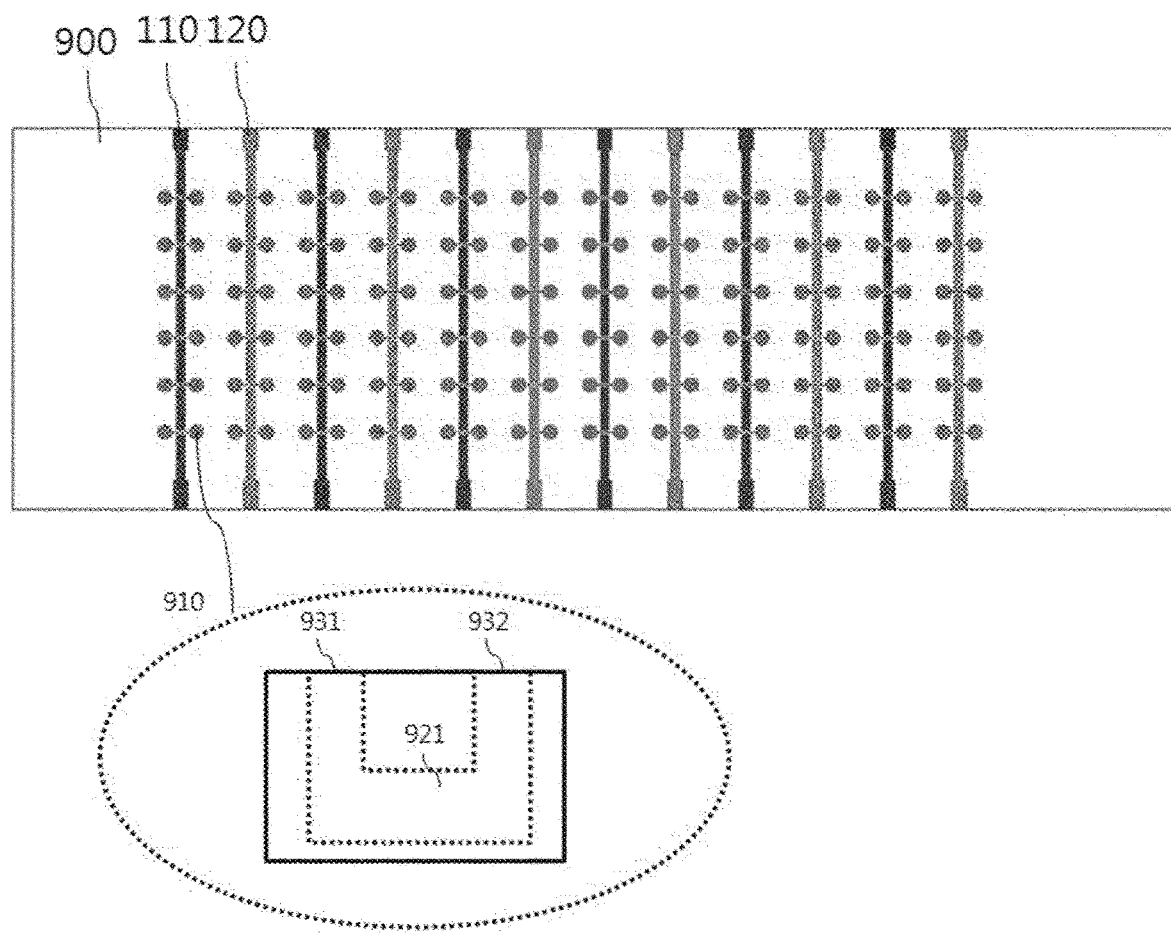
Figure 12:
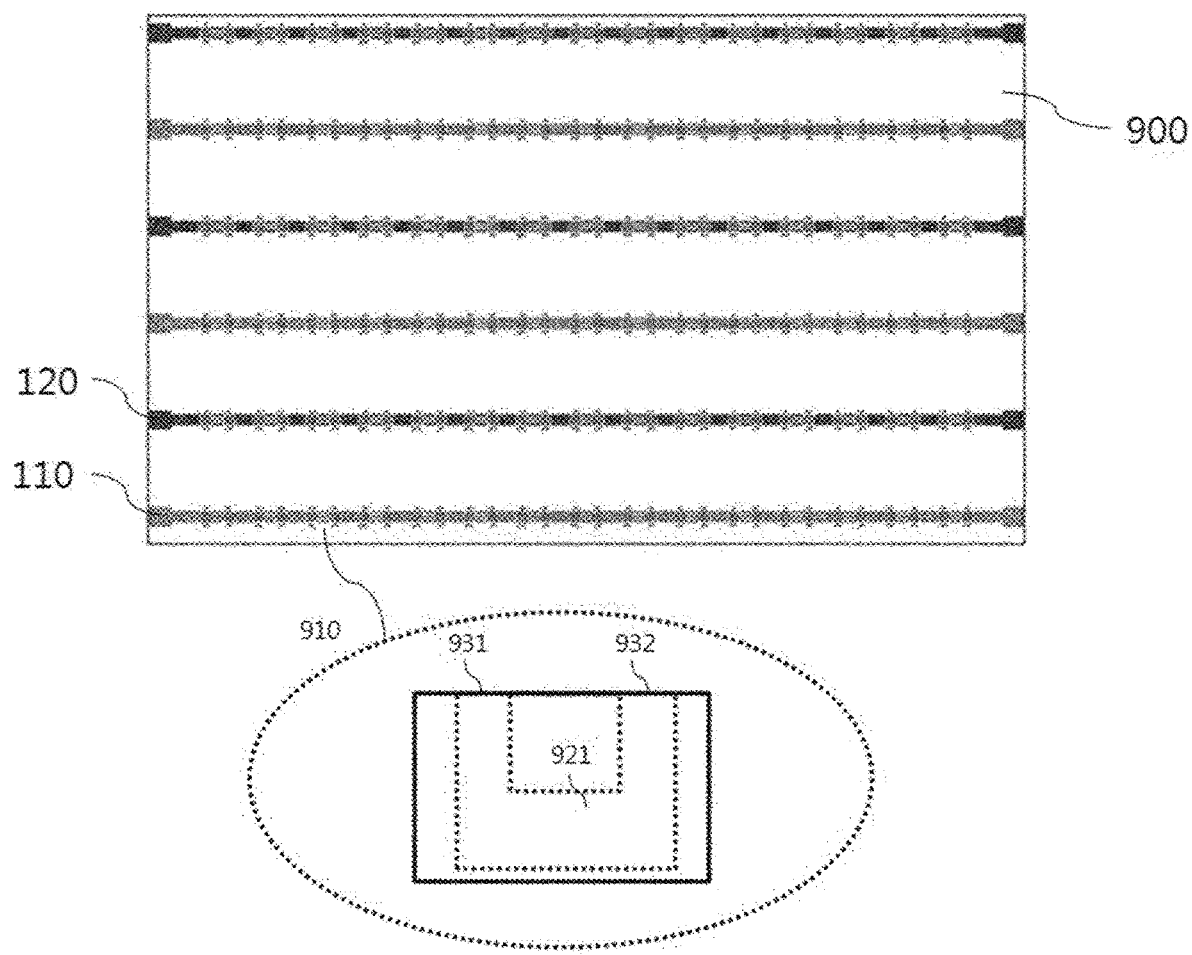

FIGS. 10 to 12 are top views showing the contacted states between the various types of PCR chip 900 and the PCR heating block in the PCR apparatus according to the present invention.

According to the present invention, as shown in FIG. 10, the PCR chip 900 includes a reaction chamber 910 in the form of an integrated type well-shaped of an inlet/outlet, and the reaction chambers 910 are arranged correspondingly to the heaters 110 and 120 of the PCR heating block 100. On the other hand, as shown in FIG. 11, the PCR chip 900 according to the present invention includes a reaction chamber 910 in the form of a separate type channel-shaped of an inlet/outlet, and the reaction chambers 910 are arranged correspondingly to the heaters 110 and 120 of the PCR heating block 100 vertically with respect to them. Furthermore, as shown in FIG. 12, the PCR chip 900 according to the present invention includes a reaction chamber 910 in the form of a separate type channel-shaped of an inlet/outlet, and the reaction chambers 910 are arranged correspondingly to the heaters 110 and 120 of the PCR heating block 100 horizontally with respect to them.

Figure 13:
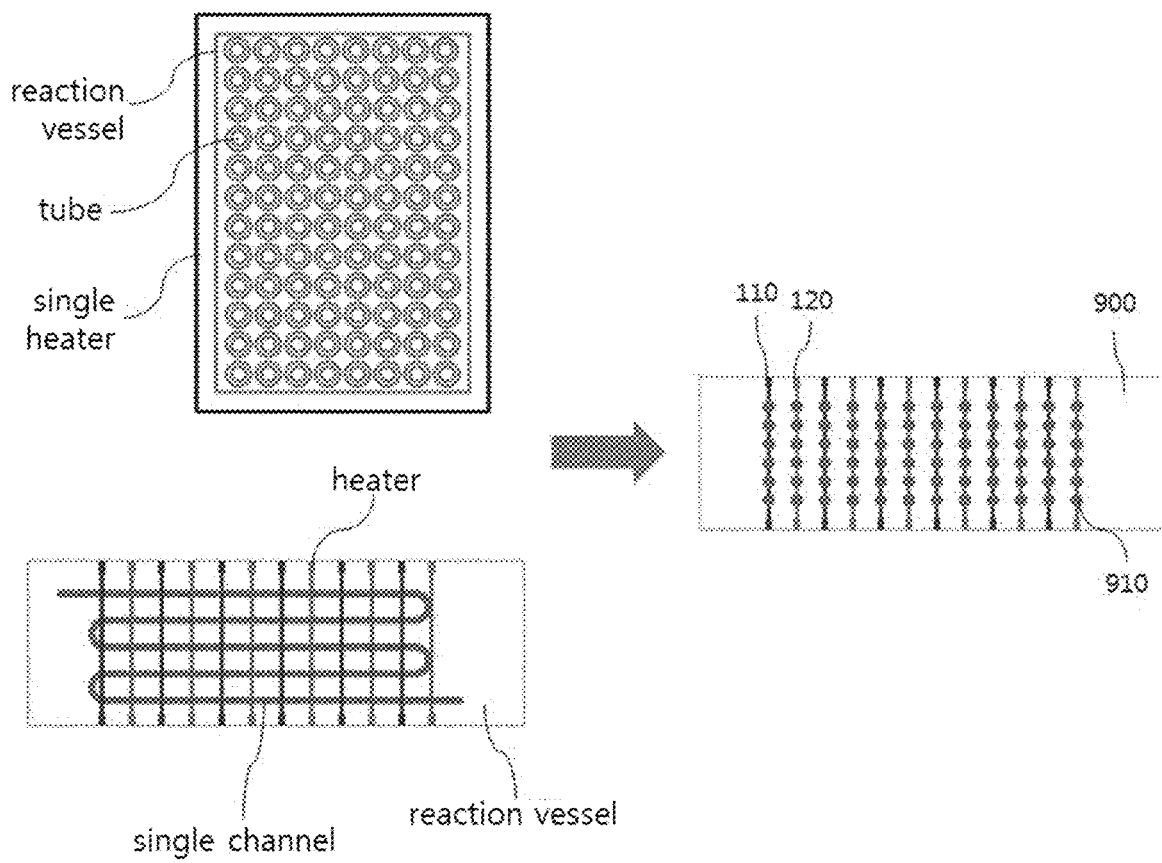
FIGS. 13 and 14 are top and sectional views showing the comparison between the existing tube and channel type PCR reaction vessels and the PCR chip in the PCR apparatus according to the present invention.
Figure 14:
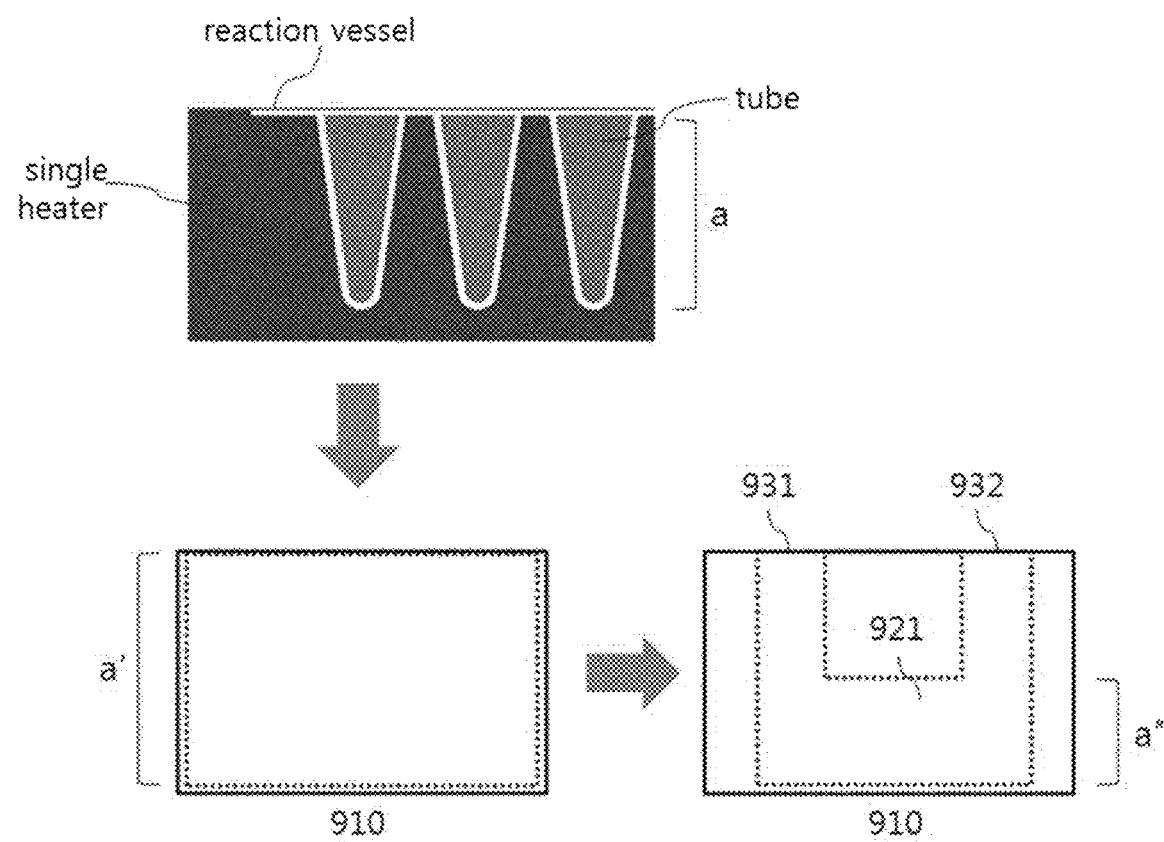

Such various types of PCR chips 900 can increase a higher density of the PCR apparatus than the conventional PCR reaction vessel, and further, they can perform the PCR efficiently. As shown in FIG. 13, the PCR chip 900 according to the present invention can at the same time perform the PCR for a larger number of various samples than those used in the conventional tube type PCR reaction vessel having a single heater, reduce the PCR time, and decrease the size of the vessel. Furthermore, the PCR chip 900 according to the present invention can at the same time perform the PCR for a larger number of various samples than those used in the conventional single channel type PCR reaction vessel having a plurality of heaters, reduce the PCR time for the plurality of samples, and greatly increase the density of the PCR apparatus because there is no separate fluid control module through the channel. On the other hand, as shown in FIG. 14, the PCR chip according to the present invention can become small-sized, thereby minimizing the amount of sample used and increasing the thermal contact surfaces between the heaters, that is, the PCR heating block and the samples to raise the surface to volume ratio ($a<a'<a''$). In this case, it is checked that the surface to volume ratios of the PCR chips as shown in FIGS. 11 and 12 are more increased than that of the PCR chip as shown in FIG. 10.

Figure 15A:
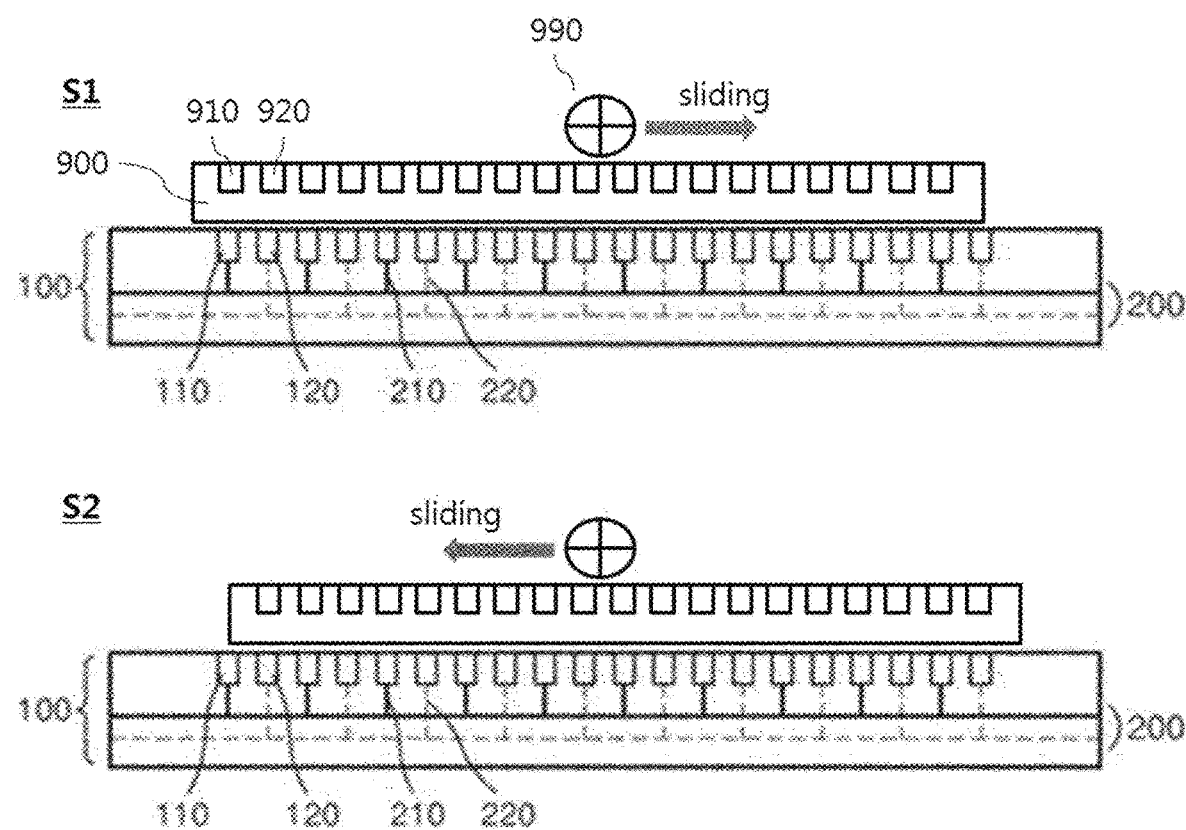
FIGS. 15a and 15b are sectional views showing repeated sliding means in the PCR apparatus according to the present invention and the PCR performance principle through the repeated sliding means.
Figure 15B:
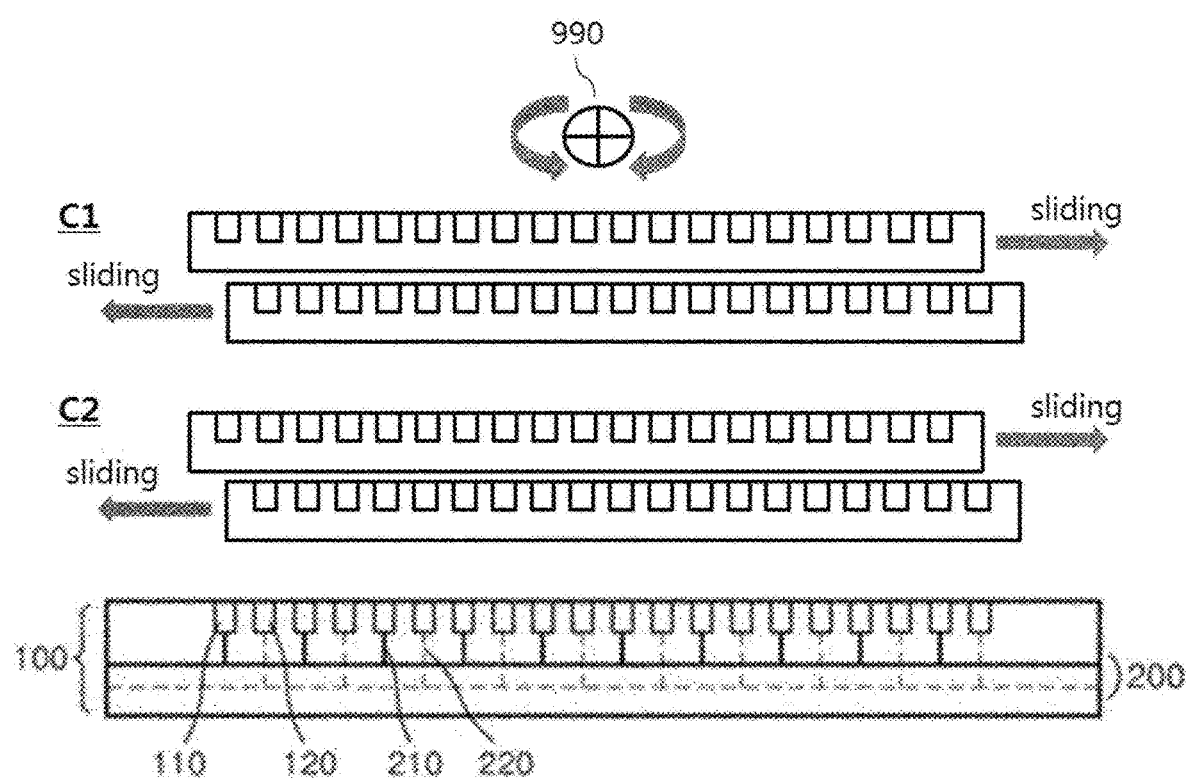

FIGS. 15*a* and 15*b* are sectional views showing the repeated sliding means in the PCR apparatus according to the present invention and the PCR principle through the repeated sliding means.

As shown in FIG. 15*a*, steps S1 and S2 in which the PCR is performed are carried out in the PCR apparatus according to the present invention having the PCR heating block 100, the power supply part 200, the PCR chip 900, and the repeated sliding means 990. The repeated sliding means 990 is simply illustrated in FIG. 15a, but it mounts the PCR chip 900 thereon to allow the PCR chip 900 to repeatedly (reciprocally) slide along the top surface of the PCR heating block 100 in such a manner as to be thermally contacted therewith. All of the reaction chambers 910 of the PCR chip 900 have the same or different PCR samples and reagents as or from each other, and the heaters 110 and 120 arranged on the PCR heating block 100 maintain the temperatures for performing the two steps for the PCR through the power supply from the power supply part 200. That is, the first heater 110 maintains a temperature of 95° C. for performing the denaturing step, and the second heater 120 maintains a temperature of 72° C. for performing the annealing/extension step. The remaining 18 heaters maintain the temperatures of 95° C. and 72° C. repeatedly.

Referring to the step S1, if the PCR chip 900 comes into thermal contact with the top surface of the PCR heating block 100, a first PCR is performed in the interiors of the reaction chambers 910 formed on the PCR chip 900, and after that, a sliding movement starts through the repeated sliding means 990. For example, when the first reaction chamber 910 formed at the end of the left side of the PCR chip 900 comes into thermal contact with the first heater 110 disposed on the end of the left side of the PCR heating block 100, the denaturing step is performed in the interior of the first reaction chamber 910. Through the right sliding movement of the repeated sliding means 990, after that, the first reaction chamber 910 comes into thermal contact with the second heater 120 disposed on the end of the left side of the PCR heating block 100.

Referring next to the step S2, if the PCR chip 900 comes into thermal contact with the top surface of the PCR heating block 100, a second PCR is performed in the interiors of the reaction chambers 910 formed on the PCR chip 900, and after that, a sliding movement starts through the repeated sliding means 990. For example, the first reaction chamber 910 formed at the end of the left side of the PCR chip 900 comes into thermal contact with the second heater 120 disposed on the end of the left side of the PCR heating block 100, the annealing/extension step is performed in the interior of the first reaction chamber 910. Through the left sliding movement of the repeated sliding means 990, after that, the first reaction chamber 910 comes into thermal contact with the first heater 110 disposed on the end of the left side of the PCR heating block 100 again. If the PCR chip 900 repeatedly (reciprocally) moves along the top surface of the PCR heating block 100 through the repeated sliding means 990 at the steps S1 and S2, one PCR cycle is finished.

As shown in FIG. 15b, the PCR cycles C1 and C2 are continuously performed through the repetition of the steps S1 and S2 as shown in FIG. 15a. The PCR apparatus according to the present invention can amplify the plurality of nucleic acid samples in a small space at the same time and rapidly and achieve the miniaturization of the apparatus through the repeated contacts between the nucleic acid samples and the heaters.

FIGS. 16a to 16h are sectional views showing the real-time PCR performed through the PCR apparatus according to the present invention.

FIGS. 16a to 16h are sectional views showing the real-time PCR performed through the PCR apparatus according to the present invention. The PCR apparatus according to the present invention includes an optical module for real-time measuring the nucleic acid amplification reactions occurring in the reaction chambers 910 of the PCR chip 900. The optical module includes light sources 150 and 1500 adapted to provide light to the reaction chambers 910 of the PCR chip 900 and light detectors 600 and 620 adapted to receive the light emitted from the PCR chip 900. In this case, a fluorescent material is added to the target sample solutions accommodated in the reaction chambers 910 of the PCR chip 900 and emits light therefrom by means of light having a specific wavelength according to the production of PCR products, thereby generating optical signals to be measurable and analyzable. The optical module may be transmissive or reflective according to the properties of the PCR chip and the PCR heating block and the arrangement types of the light sources and the light detectors. The light sources may include various kinds of light sources, and desirably, they are selected from the group consisting of mercury arc lamp, xenon arc lamp, tungsten arc lamp, metal halide arc lamp, metal halide fiber, and light-emitting diodes. Further, the light sources may have various wavelengths, and desirably, they have the wavelengths in the range of about 200 to 1300 nm, and otherwise, they have multi-wavelength through multiple light sources or filters. In this case, the light sources further include light sources by color (See FIGS. 16c and 16h). Further, the light detectors may include various kinds of light detectors, and desirably, they are selected from the group consisting of charge-coupled apparatus (CCD), charge-injection apparatus (CID), complementary-metal-oxide-semiconductor detector (CMOS), and photo multiplier tube (PMT). In this case, the light detectors further include filters by color (See FIGS. 16b, 16c, 16f, 16g and 16h). That is, the light sources and the light detectors are drivedly connected with various modules to improve the detection efficiencies. According to the present invention, for example, the light sources may further include one or more optical band pass filters capable of passing only the light having a wavelength band which can excite the fluorescent material or may be drivedly connected with one or more optical band pass filters. The optical detectors may further include one or more optical band pass filters capable of passing only the light having a wavelength band from which the fluorescent material is emitted or may be drivedly connected with one or more optical band pass filters. In this case, the light sources or the light detectors may further include substitution parts capable of allowing the excited wavelength and emitted wavelength of the fluorescent material to be detected to correspond to each other in one or more optical band pass filters or may be drivedly connected to the substitution parts. Further, the light sources may further include LEDs (Light Emitting Diodes) having one or more wavelengths so as to excite one or more fluorescent materials or may be drivedly connected to the LEDs. In this case, the light sources may further include substitution parts capable of allowing the excited wavelength and emitted wavelength of one or more fluorescent materials to correspond to each other in the LEDs or may be drivedly connected to the substitution parts.

Figure 16A:
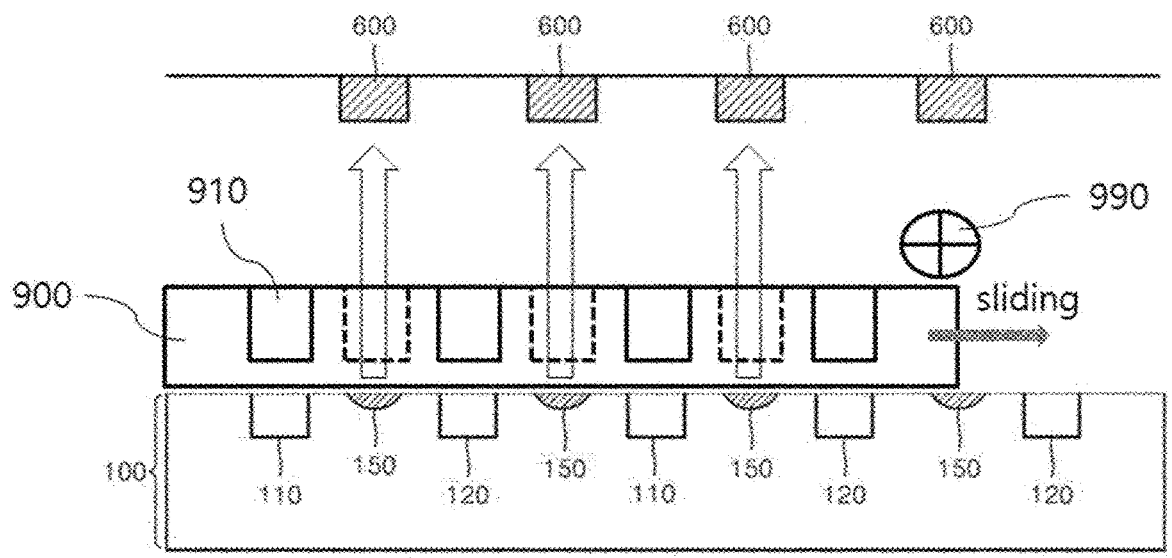
FIGS. 16a to 16h are sectional views showing the real-time PCR performed through the PCR apparatus according to the present invention.
Figure 16B:
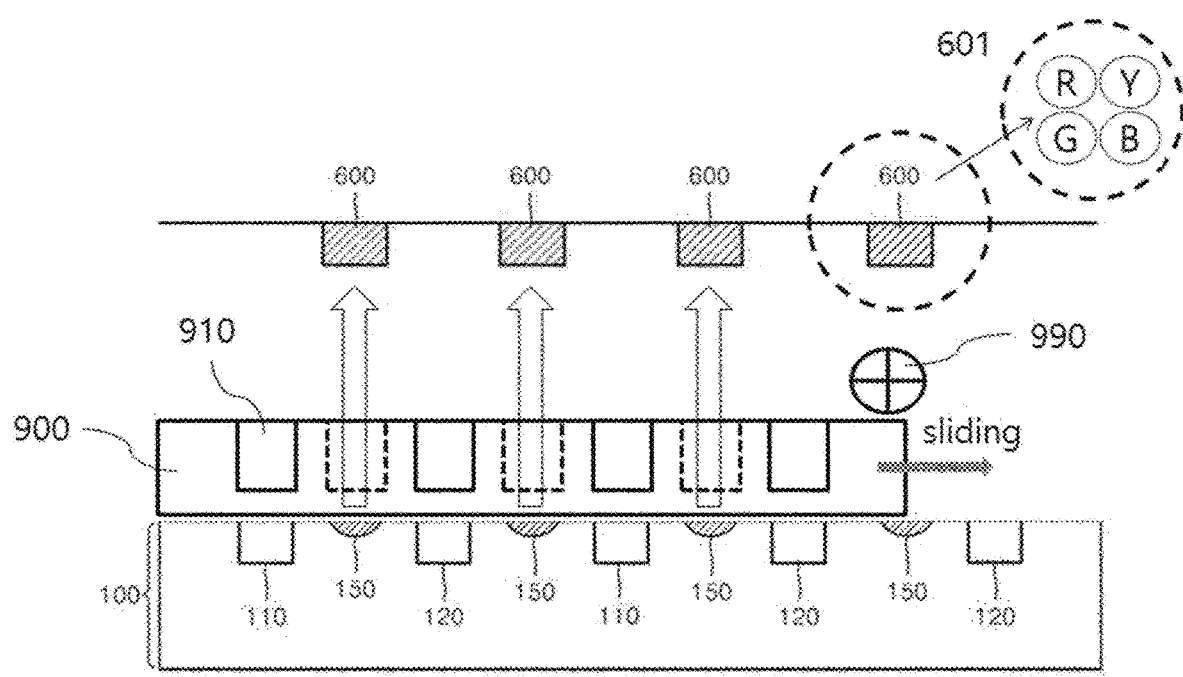
Figure 16C:
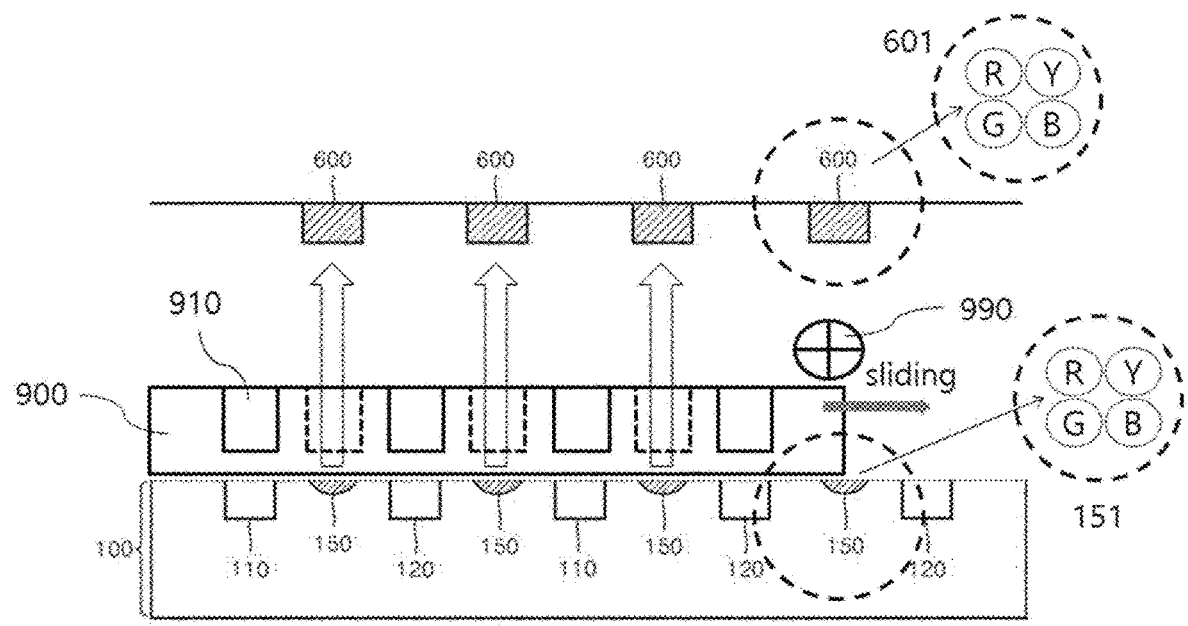
Figure 16D:
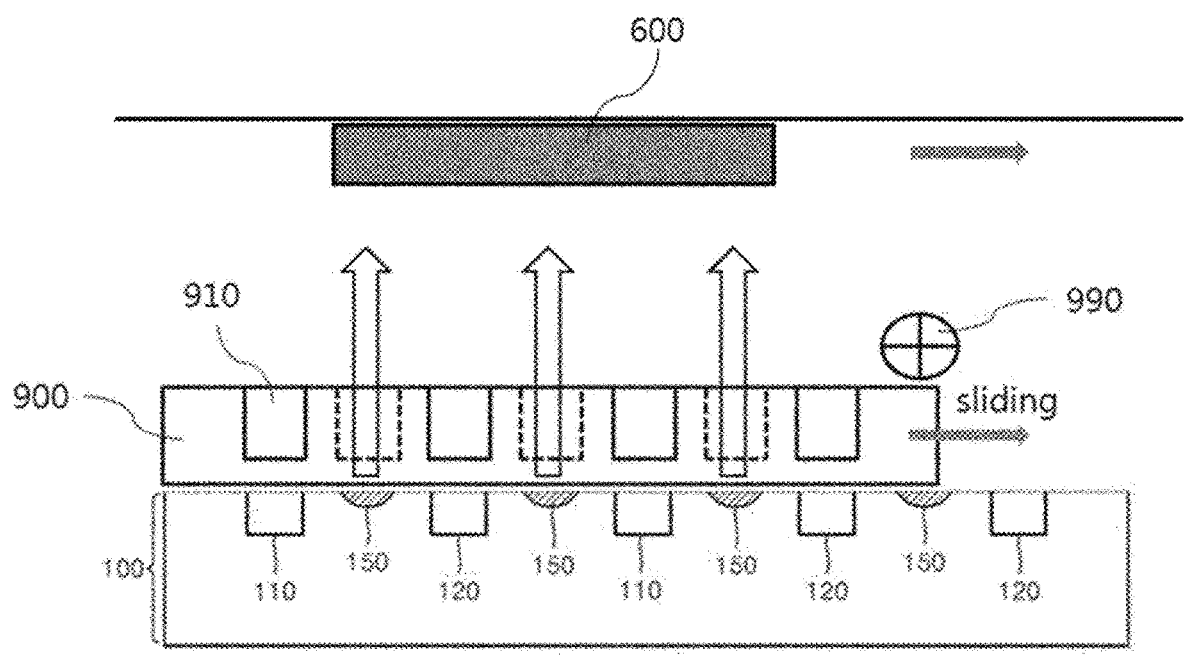

As shown in FIG. 16a, the PCR apparatus according to the present invention includes the PCR chip 900 made of a light transmissive material, the light sources 150 disposed between the first heaters 110 and the second heaters 120 of the PCR heating block 100, and the light detectors 600 adapted to detect the light signals emitted from the light sources 150. In more detail, the PCR solutions containing the target sample solutions in the reaction chambers 910 reciprocally slide along the tops of the first heaters 110 and the second heaters 120, thereby repeatedly performing the PCR denaturing step and the PCR annealing/extension step, and in this case, the target sample solutions move along the tops of the light sources 150 between the first heater 110 and the second heater 120 and between the heater units each having the first heater 110 and the second heater 120. While the reaction chambers 910 in which the target sample solutions are accommodated are moving along the tops of the light sources 150, the moving speed of the PCR chip 900 is decreased or stops for a moment through the control of the repeated sliding means 990, and after that, light is emitted from the light sources 150. The emitted light passes through the PCR chip 900, that is, the reaction chambers 910, so that the optical signals generated by the nucleic acid amplification in the reaction chambers 910 are measured and analyzed by means of the light detectors 600. During the PCR cycles, accordingly, the reaction results of the nucleic acid (coupled to the fluorescent material) amplification in the reaction chambers 910 are monitored in real time, thereby allowing the quantity of target DNA to be measured and analyzed in real time. On the other hand, FIG. 16*b* shows the PCR apparatus according to the present invention, wherein each light detector 600 has color filters 601, and FIG. 16*c* shows the PCR apparatus according to the present invention, wherein each light detector 600 has color filters 601 and each light source 150 has color light sources 151. Moreover, FIG. 16*d* shows the PCR apparatus according to the present invention, wherein the light detector 600 moves together with the PCR chip 900.

Figure 16E:
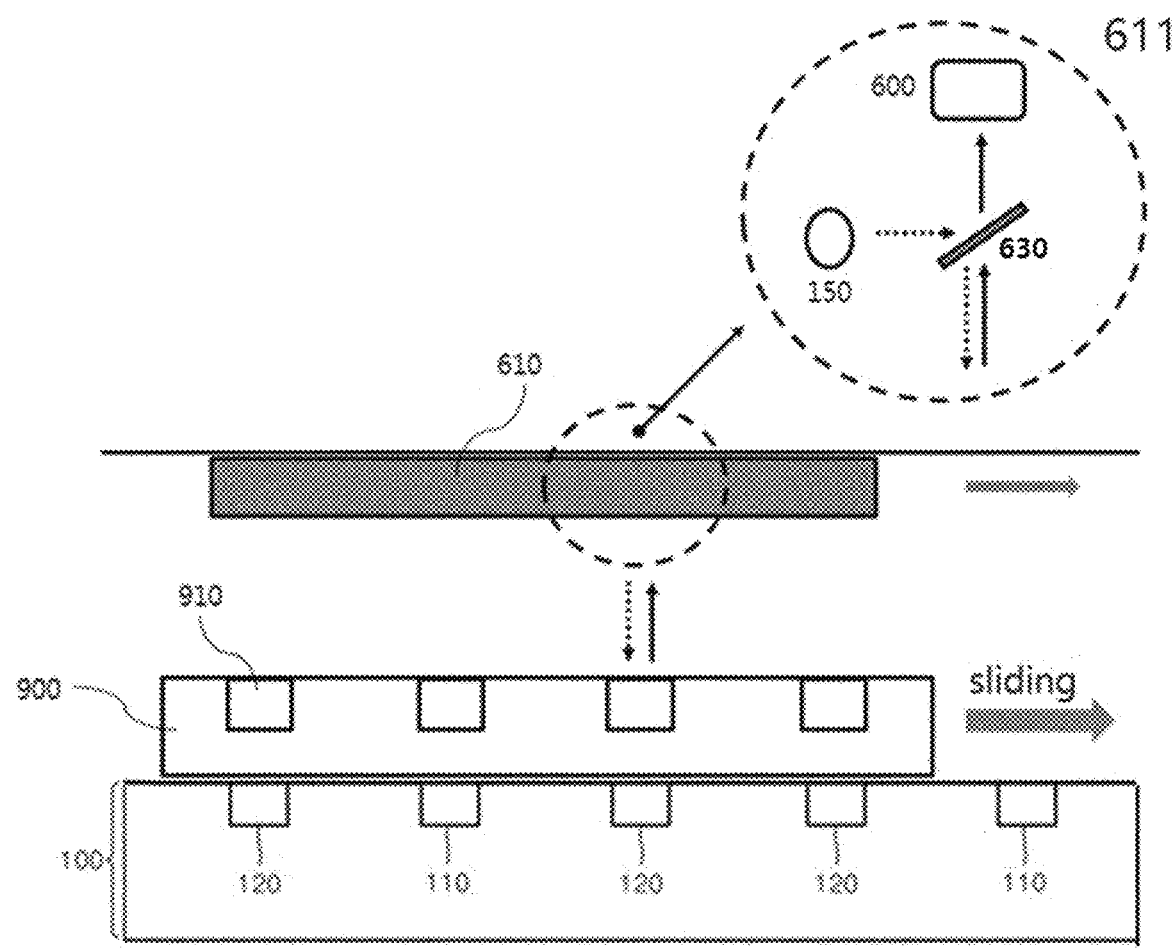
Figure 16F:
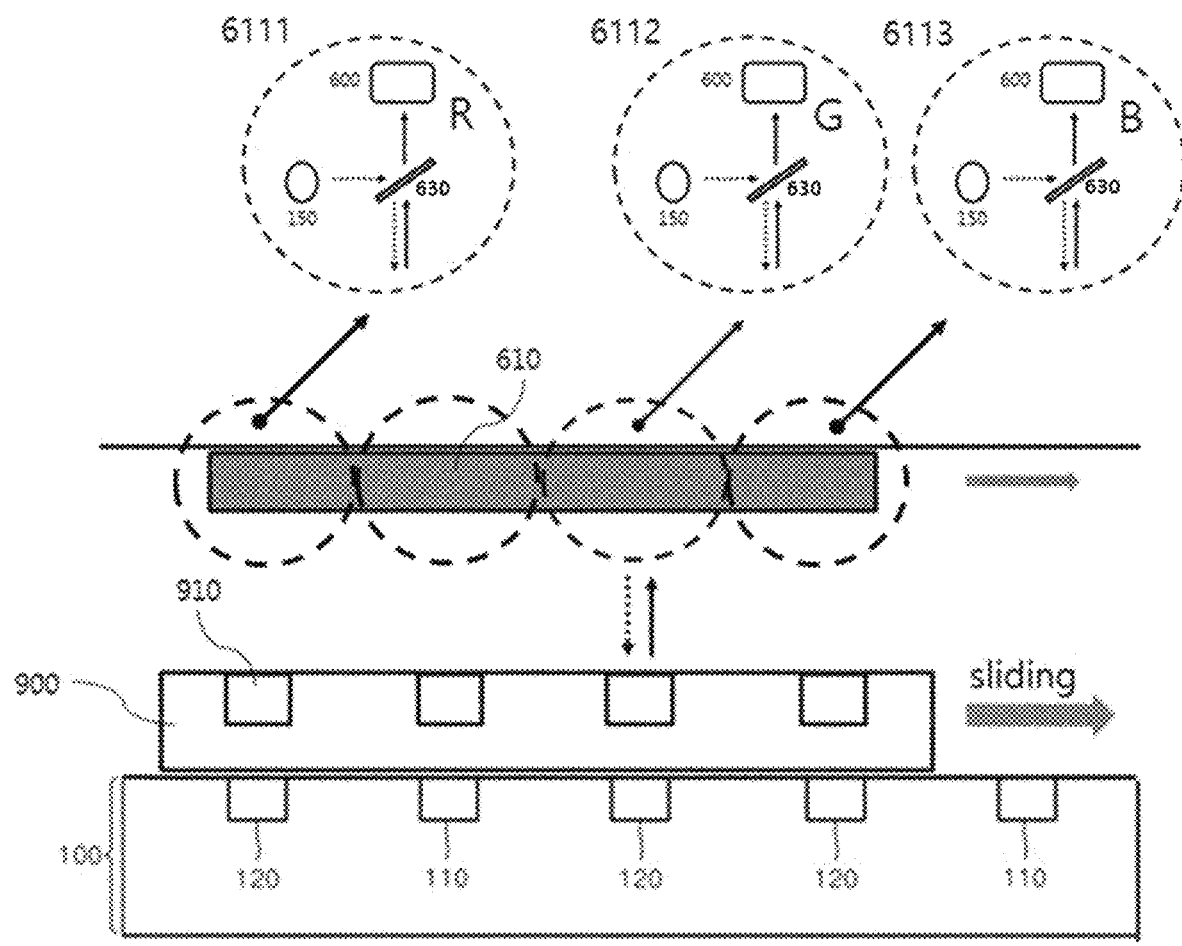

As shown in FIG. 16*e*, the PCR apparatus according to the present invention includes the PCR chip 900 made of a semi-transmissive material (made of a transmissive material on the upper layer thereof and made of a non-transmissive material on the lower layer thereof), a light source 150 moving correspondingly to the moving path of the PCR chip 900, a light detector 600 for detecting the light signal emitted from the light source 150, and an optical module 610 for transmitting the light emitted from the light source 150 to the reaction chambers 910 of the PCR chip 900 and having a dichroic mirror 630 accommodated thereinto to transmit the light emitted from the reaction chambers 910 to the light detector 600. On the other hand, FIG. 16*f* shows the PCR apparatus according to the present invention, wherein optical modules 610 include light detectors 600 having color filters.

Figure 16G:
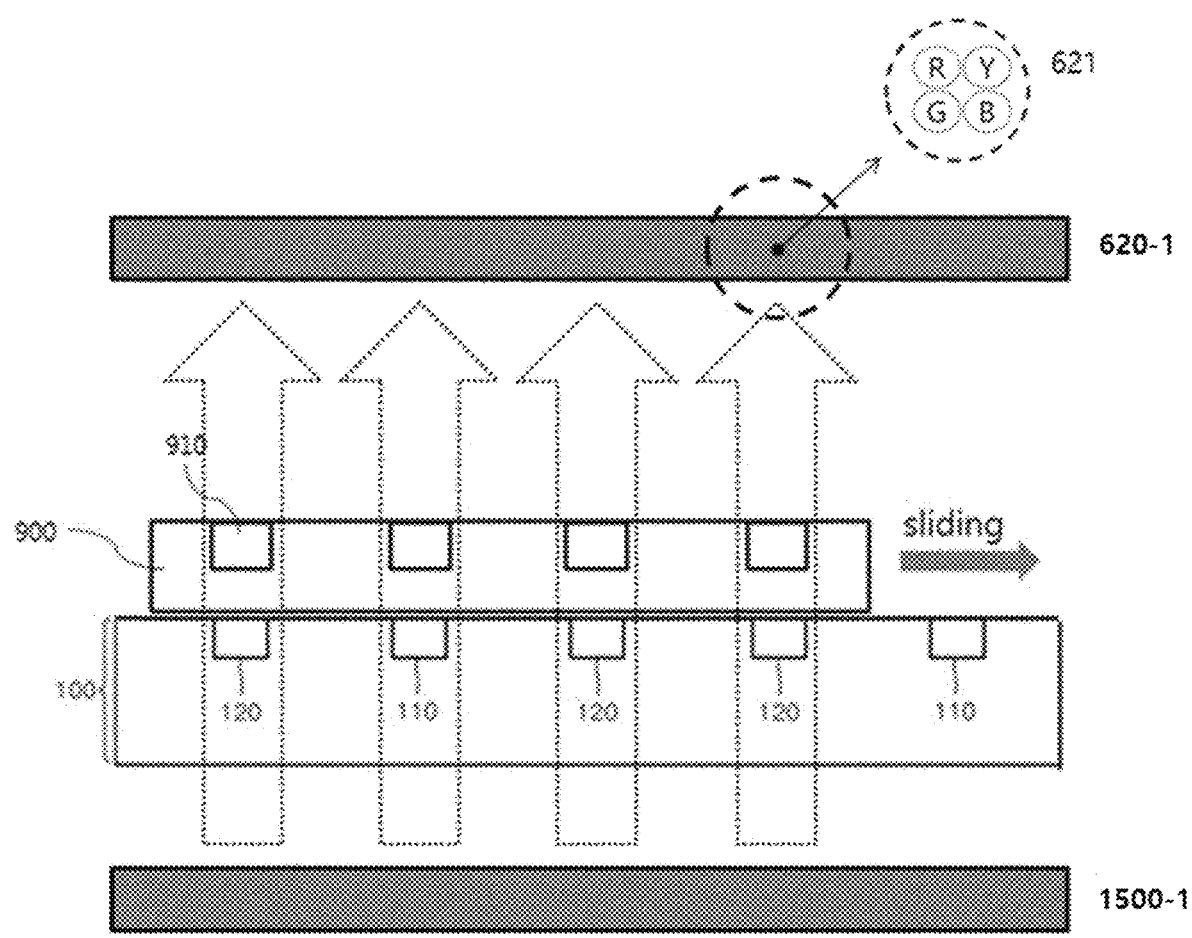
Figure 16H:
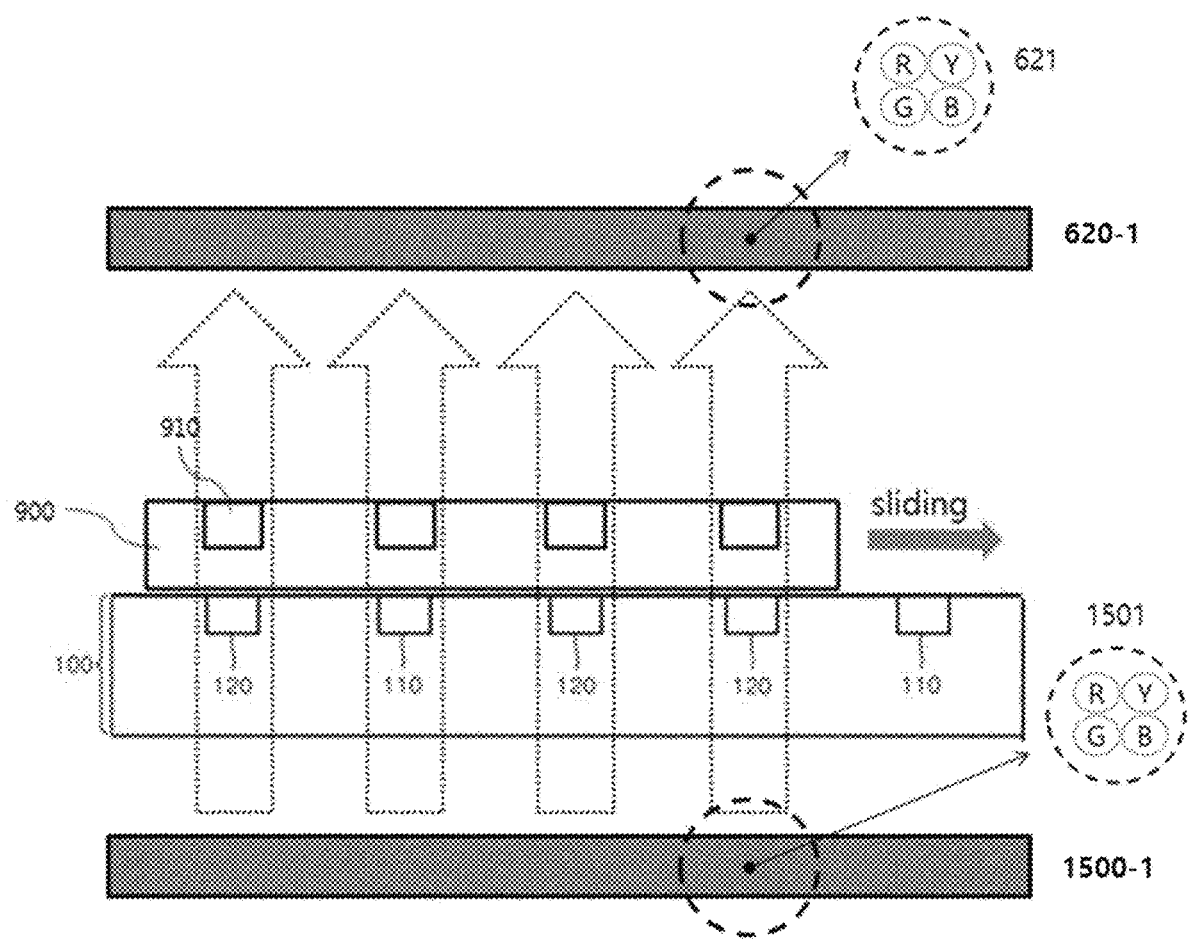

As shown in FIG. 16*g*, the PCR apparatus according to the present invention includes the PCR chip 900 made of a light transmissive material, the PCR heating block 100 made of a light transmissive material and having the first heaters 110 and the second heaters 120, a light detection module 620-1 fixedly located above the PCR chip 900, and a light source module 1500-1 fixedly located under the PCR heating block 100. In this case, the light detection module 620-1 includes light detectors located at the corresponding regions to the reaction chambers 910 of the PCR chip 900, and the light detectors have color filters 621. On the other hand, FIG. 16*h* shows the PCR apparatus according to the present invention, wherein the light detection module 620-1 includes the light detectors having the color filters 621 and the light source module 1500-1 includes color light sources 1501.

Figure 17:
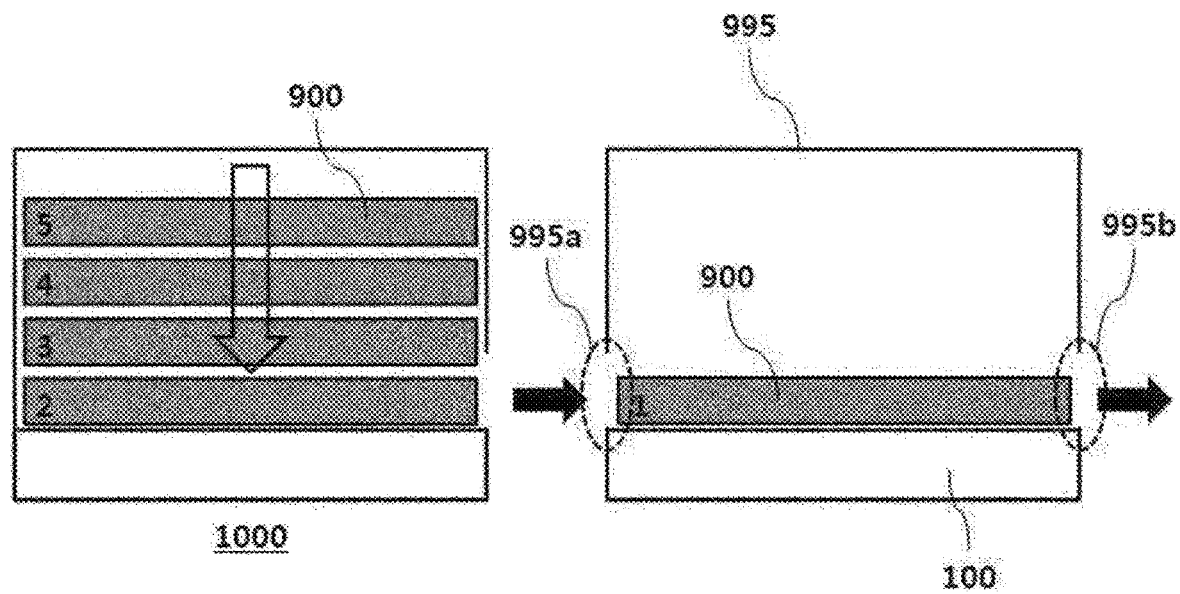
FIG. 17 is a top view showing a chip stand-by part cooperatively operated with the PCR apparatus according to the present invention.

FIG. 17 is a top view showing a chip stand-by part cooperatively operated with the PCR apparatus according to the present invention.

As shown in FIG. 17, the PCR apparatus according to the present invention further includes a chip stand-by part 1000 in which a plurality of PCR chips 900 (chip numbers 1 to 5) drivedly connected with each other is accommodated so that after the first PCR chip 900 (chip No. 1) comes into thermal contact with the PCR heating block 100, the second PCR chip 900 (chip No. 2) starts thermal contacting with the PCR heating block 100. The chip stand-by part 1000 includes the plurality of PCR chips 900 (chip numbers 1 to 5). The PCR chips accommodated in the chip stand-by part 1000 include various kinds of samples, and according to the sizes of the accommodation spaces, the larger number of PCR chips than the number of PCR chips (five PCR chips) as shown in FIG. 17 may be accommodated in the chip stand-by part 1000. For example, if the PCR heating block 100 and the first PCR chip 900 (chip No. 1) sequentially come into thermal contact with each other to start the first PCR, the first PCR chip 900 (chip No. 1) moves to the outside through a chip discharge port 995*b* of a package 995 and a chip introduction port 995*a* of the package 995 is open, so that the second PCR chip 900 (chip No. 2) accommodated in the chip stand-by part 1000 moves on the top of the PCR heating block 100 by means of separate driving means (not shown) and sequentially comes into thermal contact with the PCR heating block 100, thereby starting the second PCR. In this case, before the second PCR chip 900 (chip No. 2) passes through the chip introduction port 995*a*, it is sensed by means of a separate sensor mounted on the package 995 so that the conditions in the package 995, such as, the thermal condition of the PCR heating block 100, the reaction condition of the PCR apparatus and the like can be newly set. The above-mentioned series of processes are repeated until the PCR of the PCR chips accommodated in the chip stand-by part 1000 is completed. Through the chip stand-by part 1000, accordingly, the PCR apparatus according to the present invention can perform the PCR for the plurality of samples at the same time, sequentially and rapidly.

Figure 18:
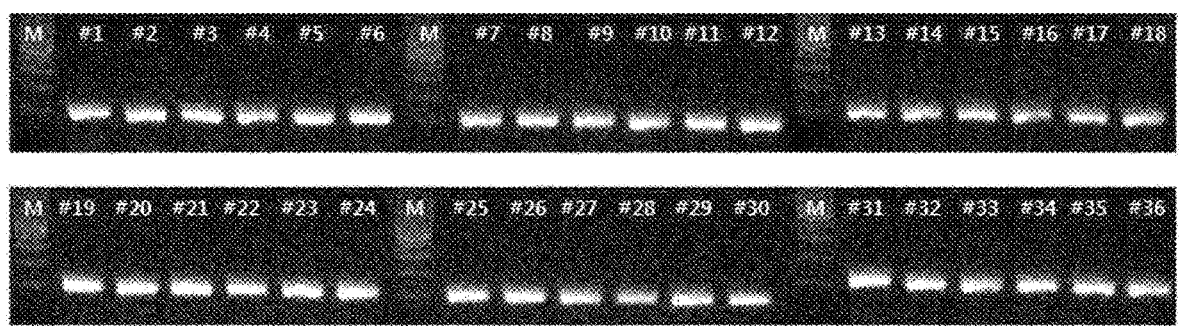
FIG. 18 is an electrophoresis photograph showing the PCR test result of the PCR apparatus according to the present invention.

FIG. 18 is an electrophoresis photograph showing the PCR test result of the PCR apparatus according to the present invention.

As shown in FIG. 18, the PCR results using the PCR apparatus according to the present invention are checked, wherein symbols "M" in the electrophoresis photograph indicate size markers and respective numbers indicate the numbers of the samples for the PCR. The PCR apparatus according to the present invention can more reduce the size of the PCR chip, the amount of sample used, and the PCR time required than the existing multi well-shaped PCR reaction vessel having the signal heater and the existing single channel-shaped PCR reaction vessel having the plurality of heaters, and further can perform the PCR for a lot of samples at the same time, thereby effectively solving the problems the existing PCR apparatuses have had.

The invention claimed is:

1. A PCR apparatus comprising:
   a PCR heating block having at least two heater units arranged on a substrate along a first direction, each of the at least two heater units having two or more heaters; and
   a PCR chip having at least two reaction chambers formed in the PCR chip,
   wherein the PCR chip is configured to repeatedly slide on the PCR heating block in a back-and-forth direction parallel to the first direction, such that the at least two reaction chambers of the PCR chip are repeatedly placed to be thermally in contact with the two or more heaters on the PCR heating block,
   wherein the PCR apparatus further comprises:
   a plurality of light sources emitting light, each of the plurality of light sources being arranged between the two or more heaters of the PCR heating block; and at least one light detector for detecting optical signals generated from the at least two reaction chambers of the PCR chip,
wherein the plurality of light sources are configured to be arranged to vertically correspond to the at least two reaction chambers with respect to the sliding direction of the PCR chip, such that the at least one light detector detects the optical signals generated from the at least two reaction chambers by the light emitted from the plurality of light sources arranged to vertically correspond to the at least two reaction chambers, and
wherein the at least one light detector is positioned above the PCR chip and configured to move corresponding to a movement route of the PCR chip.

2. The PCR apparatus of claim 1, wherein the two or more heaters in each of the at least two heater units include a first heater and a second heater, wherein the first heater has a temperature in a range of 85 to 105° C. and the second heater has a temperature in a range of 50 to 80° C.

3. The PCR apparatus of claim 1, wherein the two or more heaters in each of the at least two heater units include a first heater and a second heater, wherein the first heater has a temperature of 95° C. and the second heater has a temperature of 72° C.

4. The PCR apparatus of claim 1, wherein the two or more heaters in each of the at least two heater units include a first heater, a second heater, and a third heater, wherein the first heater has a temperature in a range of 85 to 105° C., the second heater has a temperature in a range of 40 to 60° C., and the third heater has a temperature in a range of 50 to 80° C.

5. The PCR apparatus of claim 1, wherein the two or more heaters in each of the at least two heater units include a first heater, a second heater, and a third heater, wherein the first heater has a temperature of 95° C., the second heater has a temperature of 50° C., and the third heater has a temperature of 72° C.

6. The PCR apparatus of claim 1, wherein the at least two reaction chambers of the PCR chip are disposed in the first direction or in a second direction normal to the first direction.

7. The PCR apparatus of claim 6, wherein each of the at least two reaction chambers of the PCR chip has a shape of channel extending in the second direction.

8. The PCR apparatus of claim 1, wherein the at least two reaction chambers of the PCR chip have a structure having an integrated inlet and outlet.

9. The PCR apparatus of claim 1, wherein the at least two reaction chambers of the PCR chip have a structure having a separated inlet and outlet.

10. The PCR apparatus of claim 1, further comprising a chip stand-by container adapted to accommodate a part of at least two PCR chips, wherein the at least two PCR chips have a first PCR chip and a second PCR, and wherein the chip stand-by container accommodates the first PCR chip and the second PCR, and moves each of the at least two PCR chips one after another to have a thermal contact with the PCR heating block.

11. The PCR apparatus of claim 1, further comprising a chip stand-by container comprising:
a place to accommodate a plurality of PCR chips; and
a package having,
a chip discharge port,
a chip introduction port, and
a sensor configured to detect a thermal condition of the PCR heating block, or a reaction condition of the PCR apparatus.

12. The PCR apparatus of claim 1, wherein a temperature to time ratio among the two or more heaters is in the range of 20 to 40° C. per second.

13. The PCR apparatus of claim 1, further comprising:
an optical module transmitting the light emitted from the plurality of light sources to the at least two reaction chambers of the PCR chip,
wherein the optical module has a dichroic mirror accommodated therein to transmit light emitted from the at least two reaction chambers to the at least one light detector.

14. The PCR apparatus of claim 13, wherein the at least one light detector has one or more color filters.

15. A PCR apparatus comprising:
a PCR heating block having at least two heater units arranged on a substrate along a first direction, each of the at least two heater units having two or more heaters, wherein the two or more heaters have different temperatures from one another; and
a PCR chip having at least two reaction chambers formed in the PCR chip,
wherein the PCR chip is configured to repeatedly slide on the PCR heating block in a back-and-forth direction parallel to the first direction, such that the at least two reaction chambers of the PCR chip are repeatedly placed to be thermally in contact with the two or more heaters on the PCR heating block,
wherein the PCR apparatus further comprises:
a plurality of light sources emitting light, each of the plurality of light sources being arranged between the two or more heaters of the PCR heating block; and
at least one light detector for detecting optical signals generated from the at least two reaction chambers of the PCR chip,
wherein the plurality of light sources are configured to be arranged to vertically correspond to the at least two reaction chambers with respect to the sliding direction of the PCR chip, such that the at least one light detector detects the optical signals generated from the at least two reaction chambers by the light emitted from the plurality of light sources arranged to vertically correspond to the at least two reaction chambers, and
wherein the at least one light detector is positioned above the PCR chip and configured to move corresponding to a movement route of the PCR chip.

16. The PCR apparatus of claim 15, further comprising:
an optical module transmitting the light emitted from the plurality of light sources to the at least two reaction chambers of the PCR chip,
wherein the optical module has a dichroic mirror accommodated therein to transmit light emitted from the at least two reaction chambers to the at least one light detector, and
wherein the at least one light detector has one or more color filters.

* * * * *